(12) United States Patent
Bruffey et al.

(10) Patent No.: US 8,142,508 B1
(45) Date of Patent: Mar. 27, 2012

(54) SPINAL CAGE HAVING DEPLOYABLE MEMBER WHICH IS REMOVABLE

(75) Inventors: James Bruffey, San Diego, CA (US); Eric A. Lab, Wadsworth, OH (US); Bret Everette Hartzell, Canton, OH (US); Adam C. Sclafani, Uniontown, OH (US)

(73) Assignee: Theken Spine, LLC, Akron, OH (US)

( * ) Notice: Subject to any disclaimer, the term of this patent is extended or adjusted under 35 U.S.C. 154(b) by 762 days.

(21) Appl. No.: 12/167,218

(22) Filed: Jul. 2, 2008

Related U.S. Application Data

(60) Provisional application No. 60/947,557, filed on Jul. 2, 2007, provisional application No. 61/027,260, filed on Feb. 8, 2008, provisional application No. 61/037,551, filed on Mar. 18, 2008.

(51) Int. Cl.
*A61F 2/44* (2006.01)

(52) U.S. Cl. .................................... 623/17.16

(58) Field of Classification Search .... 623/17.11–17.16; 606/246
See application file for complete search history.

(56) References Cited

U.S. PATENT DOCUMENTS

| | | |
|---|---|---|
| 5,059,193 A | 10/1991 | Kuslich |
| 5,171,278 A | 12/1992 | Pisharodi |
| 5,306,309 A | 4/1994 | Wagner et al. |
| 5,336,223 A | 8/1994 | Rogers |
| 5,431,658 A | 7/1995 | Moskovich |
| 5,484,437 A | 1/1996 | Michelson |
| 5,593,409 A | 1/1997 | Michelson |
| 5,609,635 A | 3/1997 | Michelson |
| 5,653,762 A | 8/1997 | Pisharodi |
| 5,658,335 A | 8/1997 | Allen |
| 5,658,336 A | 8/1997 | Pisharodi |
| 5,665,122 A | 9/1997 | Kambin |
| 5,683,394 A | 11/1997 | Rinner |
| 5,683,464 A | 11/1997 | Wagner et al. |
| 5,702,455 A | 12/1997 | Saggar |
| 5,722,977 A | 3/1998 | Wilhelmy |
| 5,741,253 A | 4/1998 | Michelson |
| 5,749,916 A | 5/1998 | Richelsoph |
| 5,782,830 A | 7/1998 | Farris |
| 5,782,832 A | 7/1998 | Larsen et al. |
| 5,797,909 A | 8/1998 | Michelson |
| 5,861,041 A | 1/1999 | Tienboon |
| 5,865,845 A | 2/1999 | Thalgott |
| 5,885,299 A | 3/1999 | Winslow et al. |
| 5,888,227 A | 3/1999 | Cottle |
| 5,888,228 A | 3/1999 | Knothe et al. |
| 5,899,901 A | 5/1999 | Middleton |
| 5,944,658 A | 8/1999 | Koros et al. |
| 5,976,187 A | 11/1999 | Richelsoph |
| 5,980,522 A | 11/1999 | Koros et al. |
| 6,017,342 A | 1/2000 | Rinner |
| 6,030,390 A | 2/2000 | Mehdizadeh |
| 6,042,582 A | 3/2000 | Ray |

(Continued)

FOREIGN PATENT DOCUMENTS

EP 1104665 6/2001

(Continued)

*Primary Examiner* — Nicholas Woodall
(74) *Attorney, Agent, or Firm* — Middleton Reutlinger; Robert H. Eichenberger; Eric L. Killmeier

(57) ABSTRACT

A spinal cage with a wall extending in a longitudinal direction defining an interior space is disclosed. There is also provided a deployable element in movable relation to the spinal cage.

7 Claims, 25 Drawing Sheets

U.S. PATENT DOCUMENTS

| | | | |
|---|---|---|---|
| 6,045,579 A | 4/2000 | Hochshuler et al. | |
| 6,063,088 A | 5/2000 | Winslow | |
| 6,066,175 A | 5/2000 | Henderson et al. | |
| 6,080,155 A | 6/2000 | Michelson | |
| 6,080,193 A | 6/2000 | Hochshuler et al. | |
| 6,083,225 A | 7/2000 | Winslow et al. | |
| 6,083,228 A | 7/2000 | Michelson | |
| 6,096,038 A | 8/2000 | Michelson | |
| 6,102,950 A | 8/2000 | Vaccaro | |
| 6,113,638 A | 9/2000 | Williams et al. | |
| 6,113,639 A | 9/2000 | Ray et al. | |
| 6,123,705 A | 9/2000 | Michelson | |
| 6,126,689 A | 10/2000 | Brett | |
| 6,136,031 A * | 10/2000 | Middleton | 623/17.16 |
| 6,156,037 A | 12/2000 | LeHuec et al. | |
| 6,159,211 A | 12/2000 | Boriani et al. | |
| 6,159,215 A | 12/2000 | Urbahns et al. | |
| 6,159,244 A | 12/2000 | Suddaby | |
| 6,159,245 A | 12/2000 | Meriwether et al. | |
| 6,174,334 B1 | 1/2001 | Suddaby | |
| 6,179,873 B1 | 1/2001 | Zientek | |
| 6,183,517 B1 | 2/2001 | Suddaby | |
| 6,193,755 B1 | 2/2001 | Metz-Stavenhagen et al. | |
| 6,193,757 B1 | 2/2001 | Foley et al. | |
| 6,200,348 B1 | 3/2001 | Biedermann et al. | |
| 6,206,922 B1 | 3/2001 | Zdeblick et al. | |
| 6,224,599 B1 | 5/2001 | Baynham et al. | |
| 6,224,607 B1 | 5/2001 | Michelson | |
| 6,235,059 B1 | 5/2001 | Benezech et al. | |
| 6,245,108 B1 | 6/2001 | Biscup | |
| 6,251,140 B1 | 6/2001 | Marino et al. | |
| 6,261,296 B1 | 7/2001 | Aebi et al. | |
| 6,267,763 B1 | 7/2001 | Castro | |
| 6,270,498 B1 | 8/2001 | Michelson | |
| 6,277,122 B1 | 8/2001 | McGahan et al. | |
| 6,283,966 B1 | 9/2001 | Houfburg | |
| 6,290,724 B1 | 9/2001 | Marino | |
| 6,302,914 B1 | 10/2001 | Michelson | |
| 6,319,257 B1 | 11/2001 | Carignan et al. | |
| 6,332,887 B1 | 12/2001 | Knox | |
| 6,332,895 B1 | 12/2001 | Suddaby | |
| 6,364,880 B1 | 4/2002 | Michelson | |
| 6,371,987 B1 | 4/2002 | Weiland et al. | |
| 6,409,766 B1 | 6/2002 | Brett | |
| 6,419,705 B1 | 7/2002 | Erickson | |
| 6,423,095 B1 | 7/2002 | Van Hoeck et al. | |
| 6,428,541 B1 | 8/2002 | Boyd et al. | |
| 6,428,544 B1 | 8/2002 | Ralph et al. | |
| 6,432,106 B1 | 8/2002 | Fraser | |
| 6,436,098 B1 | 8/2002 | Michelson | |
| 6,436,101 B1 | 8/2002 | Hamada | |
| 6,447,512 B1 | 9/2002 | Landry et al. | |
| 6,447,544 B1 | 9/2002 | Michelson | |
| 6,454,805 B1 | 9/2002 | Baccelli et al. | |
| 6,454,806 B1 | 9/2002 | Cohen et al. | |
| 6,458,159 B1 | 10/2002 | Thalgott | |
| 6,468,311 B2 | 10/2002 | Boyd et al. | |
| 6,478,800 B1 | 11/2002 | Fraser et al. | |
| 6,478,801 B1 | 11/2002 | Ralph et al. | |
| 6,478,823 B1 | 11/2002 | Michelson | |
| 6,482,233 B1 | 11/2002 | Aebi et al. | |
| 6,488,710 B2 | 12/2002 | Besselink | |
| 6,491,724 B1 | 12/2002 | Ferree | |
| 6,500,180 B1 | 12/2002 | Foley et al. | |
| 6,517,544 B1 | 2/2003 | Michelson | |
| 6,527,803 B1 | 3/2003 | Crozet et al. | |
| 6,537,279 B1 | 3/2003 | Michelson | |
| 6,551,316 B1 | 4/2003 | Rinner et al. | |
| 6,562,074 B2 | 5/2003 | Gerbec et al. | |
| 6,565,574 B2 | 5/2003 | Michelson | |
| 6,569,168 B2 | 5/2003 | Lin | |
| 6,582,431 B1 | 6/2003 | Ray | |
| 6,585,749 B2 | 7/2003 | Hanson | |
| 6,589,247 B2 | 7/2003 | McGahan et al. | |
| 6,599,291 B1 | 7/2003 | Foley et al. | |
| 6,599,292 B1 | 7/2003 | Ray | |
| 6,607,559 B2 | 8/2003 | Ralph et al. | |
| 6,635,086 B2 | 10/2003 | Lin | |
| 6,641,582 B1 | 11/2003 | Hanson et al. | |
| 6,641,614 B1 | 11/2003 | Wagner et al. | |
| 6,648,917 B2 | 11/2003 | Gerbec et al. | |
| 6,652,533 B2 | 11/2003 | O'Neil | |
| 6,666,866 B2 | 12/2003 | Martz et al. | |
| 6,676,703 B2 | 1/2004 | Biscup | |
| 6,706,070 B1 | 3/2004 | Wagner et al. | |
| 6,712,819 B2 | 3/2004 | Zucherman et al. | |
| 6,712,825 B2 | 3/2004 | Aebi et al. | |
| 6,719,796 B2 | 4/2004 | Cohen et al. | |
| 6,730,126 B2 | 5/2004 | Boehm, Jr. et al. | |
| 6,740,088 B1 | 5/2004 | Kozak et al. | |
| 6,743,255 B2 | 6/2004 | Ferree | |
| 6,746,450 B1 | 6/2004 | Wall et al. | |
| 6,746,454 B2 | 6/2004 | Winterbottom et al. | |
| 6,749,635 B1 * | 6/2004 | Bryan | 623/17.16 |
| 6,755,841 B2 | 6/2004 | Fraser et al. | |
| 6,758,849 B1 | 7/2004 | Michelson | |
| 6,767,367 B1 * | 7/2004 | Michelson | 623/17.16 |
| 6,770,074 B2 | 8/2004 | Michelson | |
| 6,770,096 B2 | 8/2004 | Bolger et al. | |
| 6,793,658 B2 | 9/2004 | LeHuec et al. | |
| 6,824,565 B2 | 11/2004 | Muhanna et al. | |
| 6,827,740 B1 | 12/2004 | Michelson | |
| 6,830,589 B2 | 12/2004 | Erickson | |
| 6,840,941 B2 | 1/2005 | Rogers et al. | |
| 6,852,129 B2 | 2/2005 | Gerbec et al. | |
| 6,855,148 B2 | 2/2005 | Foley et al. | |
| 6,863,673 B2 | 3/2005 | Gerbec et al. | |
| 6,875,213 B2 | 4/2005 | Michelson | |
| 6,884,242 B2 | 4/2005 | LeHuec et al. | |
| 6,893,464 B2 | 5/2005 | Kiester | |
| 6,902,566 B2 | 6/2005 | Zucherman et al. | |
| 6,923,830 B2 | 8/2005 | Michelson | |
| 6,929,647 B2 | 8/2005 | Cohen | |
| 6,955,691 B2 | 10/2005 | Chae et al. | |
| 6,966,912 B2 | 11/2005 | Michelson | |
| 6,974,480 B2 | 12/2005 | Messerli et al. | |
| 6,976,988 B2 | 12/2005 | Ralph et al. | |
| 6,981,975 B2 | 1/2006 | Michelson | |
| 6,986,772 B2 | 1/2006 | Michelson | |
| 7,004,947 B2 | 2/2006 | Shluzas | |
| 7,018,415 B1 | 3/2006 | McKay | |
| 7,018,416 B2 | 3/2006 | Hanson et al. | |
| 7,033,394 B2 | 4/2006 | Michelson | |
| 7,041,135 B2 | 5/2006 | Michelson | |
| 7,051,417 B2 | 5/2006 | Michelson | |
| 7,066,961 B2 | 6/2006 | Michelson | |
| 7,070,598 B2 | 7/2006 | Lim et al. | |
| 7,077,864 B2 | 7/2006 | Byrd, III et al. | |
| 7,081,118 B2 | 7/2006 | Weber | |
| 7,083,650 B2 | 8/2006 | Moskowitz et al. | |
| 7,087,055 B2 | 8/2006 | Lim et al. | |
| 7,094,257 B2 | 8/2006 | Mujwid et al. | |
| 7,108,698 B2 | 9/2006 | Robbins | |
| 7,112,206 B2 | 9/2006 | Michelson | |
| 7,112,224 B2 | 9/2006 | Liu | |
| 7,115,132 B2 | 10/2006 | Errico | |
| 7,115,143 B1 | 10/2006 | Michelson | |
| 7,118,579 B2 | 10/2006 | Michelson | |
| 7,135,043 B2 | 11/2006 | Nakahara et al. | |
| 7,137,997 B2 | 11/2006 | Paul | |
| 7,144,275 B2 | 12/2006 | Iida | |
| 7,153,303 B2 | 12/2006 | Squires | |
| 7,153,304 B2 | 12/2006 | Robie et al. | |
| 7,160,304 B2 | 1/2007 | Michelson | |
| 7,163,561 B2 | 1/2007 | Michelson | |
| 7,166,129 B2 | 1/2007 | Michelson | |
| 7,166,130 B2 | 1/2007 | Ferree | |
| 7,169,152 B2 | 1/2007 | Foley | |
| 7,169,153 B2 | 1/2007 | Keller | |
| 7,169,182 B2 | 1/2007 | Errico et al. | |
| 7,172,627 B2 * | 2/2007 | Fiere et al. | 623/17.11 |
| 7,189,242 B2 | 3/2007 | Boyd et al. | |
| 7,189,244 B2 | 3/2007 | Newton | |
| 7,207,991 B2 | 4/2007 | Michelson | |
| 7,211,085 B2 | 5/2007 | Michelson | |
| 7,211,100 B2 | 5/2007 | Hanson | |
| 7,217,292 B2 | 5/2007 | Ralph et al. | |

| | | |
|---|---|---|
| 7,217,293 B2 | 5/2007 | Branch, Jr. |
| 7,229,477 B2 | 6/2007 | Biscup |
| 7,232,463 B2 | 6/2007 | Falahee |
| 7,235,081 B2 | 6/2007 | Errico et al. |
| 7,235,082 B2 | 6/2007 | Bartish |
| 7,244,275 B2 | 7/2007 | Michelson |
| 7,255,698 B2 | 8/2007 | Michelson |
| 7,288,093 B2 | 10/2007 | Michelson |
| 7,288,095 B2 | 10/2007 | Baynham et al. |
| 7,303,565 B2 | 12/2007 | Buttermann |
| 2002/0128713 A1 | 9/2002 | Ferree |
| 2003/0023312 A1* | 1/2003 | Thalgott .................... 623/17.16 |
| 2003/0040798 A1 | 2/2003 | Michelson |
| 2004/0117020 A1* | 6/2004 | Frey et al. .................. 623/17.11 |
| 2004/0153156 A1 | 8/2004 | Cohen |
| 2004/0215198 A1 | 10/2004 | Marnay |
| 2005/0021041 A1 | 1/2005 | Michelson |
| 2005/0080422 A1 | 4/2005 | Otte |
| 2005/0087628 A1 | 4/2005 | Sayar |
| 2005/0107878 A1 | 5/2005 | Conchy |
| 2005/0187628 A1 | 8/2005 | Michelson |
| 2005/0216083 A1 | 9/2005 | Michelson |
| 2005/0283236 A1 | 12/2005 | Razian |
| 2006/0036247 A1 | 2/2006 | Michelson |
| 2006/0058793 A1 | 3/2006 | Michelson |
| 2006/0058876 A1 | 3/2006 | McKinley |
| 2006/0058878 A1 | 3/2006 | Michelson |
| 2006/0069442 A1 | 3/2006 | Michelson |
| 2006/0079962 A1 | 4/2006 | Michelson |
| 2006/0085001 A1 | 4/2006 | Michelson |
| 2006/0100633 A1 | 5/2006 | Michelson |
| 2006/0106395 A1 | 5/2006 | Link |
| 2006/0116768 A1* | 6/2006 | Krueger et al. ............ 623/17.14 |
| 2006/0122701 A1 | 6/2006 | Kiester |
| 2006/0200138 A1 | 9/2006 | Michelson |
| 2006/0200164 A1 | 9/2006 | Michelson |
| 2006/0206207 A1 | 9/2006 | Dryer et al. |
| 2006/0241764 A1 | 10/2006 | Michelson |
| 2006/0265077 A1 | 11/2006 | Zwirkoski |
| 2007/0032871 A1 | 2/2007 | Michelson |
| 2007/0055376 A1 | 3/2007 | Michelson |
| 2007/0100452 A1* | 5/2007 | Prosser ....................... 623/17.11 |
| 2007/0276370 A1 | 11/2007 | Altarac |
| 2007/0288007 A1 | 12/2007 | Burkus et al. |
| 2007/0293949 A1 | 12/2007 | Salerni |
| 2008/0027550 A1 | 1/2008 | Link et al. |
| 2008/0103501 A1 | 5/2008 | Ralph et al. |
| 2010/0305704 A1 | 12/2010 | Messerli et al. |

FOREIGN PATENT DOCUMENTS

| | | |
|---|---|---|
| EP | 1338257 | 8/2003 |
| EP | 1374809 | 1/2004 |
| FR | 2880795 | 1/2005 |
| FR | 2880795 A1 * | 7/2006 |
| JP | 2010051651 A * | 3/2010 |
| WO | WO 2010037926 | 4/2010 |

* cited by examiner

SPINAL CAGE HAVING DEPLOYABLE MEMBER WHICH IS REMOVABLE

CROSS-REFERENCE TO RELATED DOCUMENTS

This application claims priority to and benefit under 35 U.S.C. §119(e) to copending U.S. Provisional App. Nos. 60/947,557, filed Jul. 2, 2007 and entitled "Spinal Cage having Deployable Member which is Removable;" 61/027,260, filed Feb. 8, 2008 and entitled "Spinal Cage Having Deployable Member which is Removable;" and to 61/037,551, filed on Mar. 18, 2008 and entitled "Spinal Fusion Device." The entire contents of these provisional applications are herein incorporated by reference.

TECHNICAL FIELD

This invention pertains to surgery, such as spinal surgery.

BACKGROUND

Spinal cages are used for spinal fusion (arthrodesis). Sometimes, spinal cages have been used in conjunction with a separate plate that is attached to at least one of the vertebrae involved in the fusion and has physically prevented possible motion of the spinal cage away from its intended position.

SUMMARY

A first exemplary embodiment of the present invention is provided with a spinal cage having a wall extending in a longitudinal direction. The wall progresses circumferentially in a closed curve within an envelope of a vertebral cross-section. The closed curve defines an interior space.

Another exemplary embodiment of the present invention is provided with a spinal cage having a structure to space vertebrae apart from each other. The embodiment is also provided with a recess facing an interior of the spinal cage and a shaft recess within the recess.

Yet another exemplary embodiment of the present invention is provided with a spinal cage with a bendable member and a rigid structure.

Another exemplary embodiment of the present invention is provides a spin plate having a blade and a shaft. The blade and shaft being sized to fit within a spinal cage. The spin plate may be rotatable with respect to the cage.

Still another exemplary embodiment of the present invention provides a spinal cage assembly having a spinal cage and a spin plate. A wall of the spinal cage extends in a longitudinal direction. The wall progresses circumferentially in a closed curve within an envelope of a vertebral cross-section. The closed curve defines an interior space. The spin plate is engageable with the spinal cage.

Still another exemplary embodiment of the present invention provides a spinal cage assembly having a spinal cage and a deployable member. A wall of the spinal cage extends in a longitudinal direction. The wall progresses circumferentially in a closed curve within an envelope of a vertebral cross-section. The closed curve defines an interior space. The deployable member is engageable with the spinal cage.

Another embodiment of the present invention provides an assembly having a first spinal cage, a second spinal cage, and a spacer between the cages. At least one of the cages is provided with a spin-plate.

Yet another embodiment provides a kit with a spinal cage and a spin plate. The spin plate being suitable to engage with the spinal cage. The kit may also be provided with a filler piece.

Yet another embodiment of the present invention provides a spinal cage and filler piece assembly. The assembly is provided with a spinal cage with an internal space, and a filler piece with a geometry to be placed in the internal space.

Another embodiment of the present invention provides a spinal cage with at least three instrumentation interfaces on an external surface. Each of the instrumentation interfaces being configured for use with a different surgical approach.

Another embodiment of the present invention provides a spinal cage with at least two instrumentation interfaces on an external surface. Each of the instrumentation interfaces being configured for use with a different surgical approach.

Another embodiment of the present invention provides an installation set having a spinal implant with a rotatable member, a first installation tool and a second installation tool. The first installation tool is engageable with the spinal implant and the second installation tool is capable of turning the rotatable member.

Another embodiment of the present invention provides a surgical procedure with a first step of creating a first surgical approach. A second step of implanting a spinal implant with a deployable member through the first approach. A third step of creating a second surgical approach. And a fourth step of deploying the deployable member.

Another embodiment of the present invention provides a trial piece for spinal surgery having a rigid body and a deployable member.

Another embodiment of the present invention provides another surgical procedure that is provided with a trial piece having a deployable member and a spinal cage with a deployable member. The procedure is provided with the steps of: implanting the trial piece and deploying its deployable member; retracting the deployable member and removing the trial piece; implanting the spinal cage and deploying its deployable member.

Another embodiment of the present invention provides a spinal cage assembly with a spinal cage, a spin-plate, and a gear associated with the spin-plate.

Another embodiment of the present invention provides an installation tool for a spinal cage with a deployable member. The tool is provided with a first member for interfacing with the spinal cage and a second member for interfacing with the deployable member.

Another embodiment of the present invention provides a spinal cage assembly and installation tool set. The spinal cage assembly is provided with a spinal cage, a spin-plate rotatable with respect to the spinal cage. The installation tool is capable of engaging the spinal cage and further capable of engaging the spin-plate and rotating the spin plate relative to the spinal cage.

BRIEF DESCRIPTION OF THE ILLUSTRATIONS

Embodiments of the invention are illustrated in the following illustrations.

FIG. 6b is a cross-section of FIG. 6a.

Figure 7A:
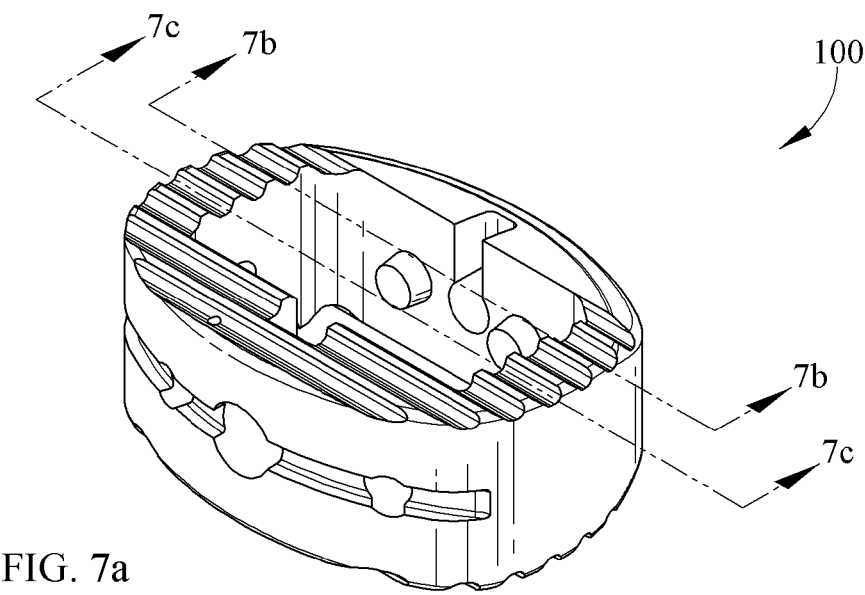
Figure 7B:
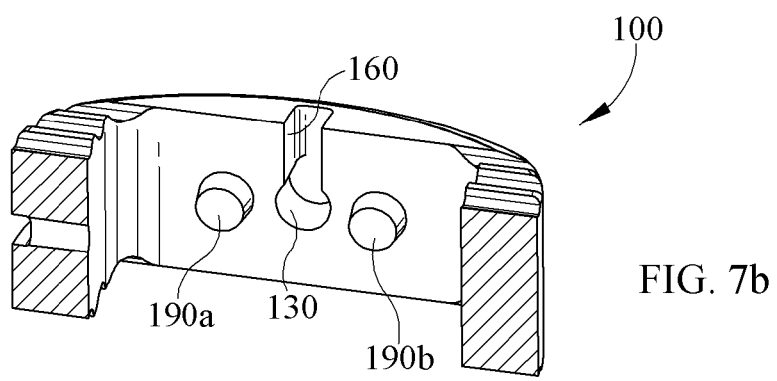
Figure 7C:
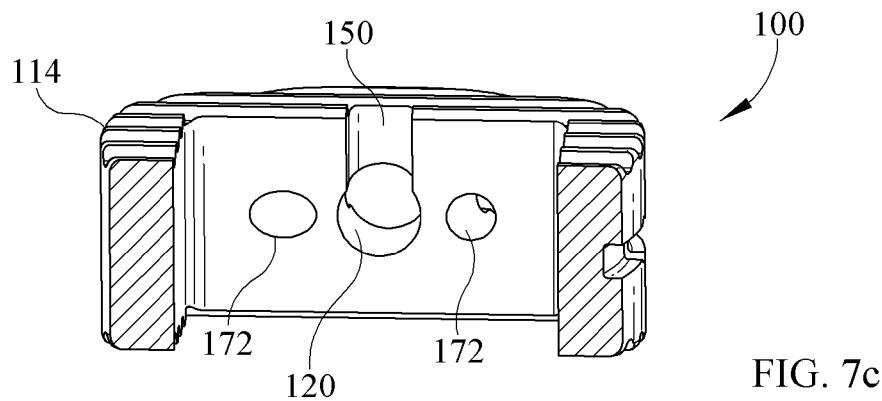

FIG. 7a is a three-dimensional illustration of the spinal cage for purposes of orienting FIG. 7b and FIG. 7c. FIG. 7b is a three-dimensional illustration that is a close-up of a feature on one internal surface of the spinal cage, for interacting with the spin-plate. FIG. 7c is a three-dimensional illustration that is a close-up of a feature on another internal surface of the spinal cage, for interacting with the spin-plate.

Figure 8A:
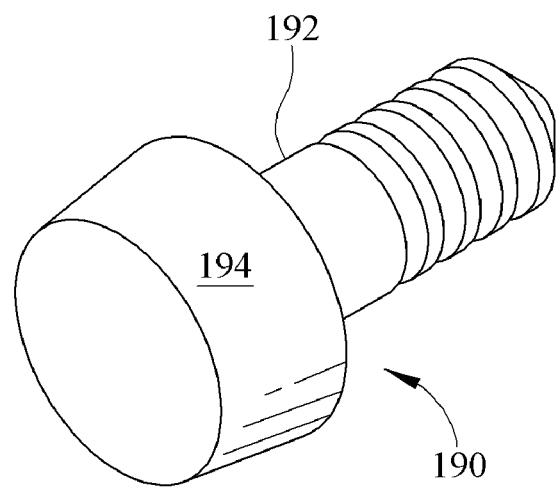

FIG. 8a is a three-dimensional illustration of a post for the spinal cage.

Figure 8B:
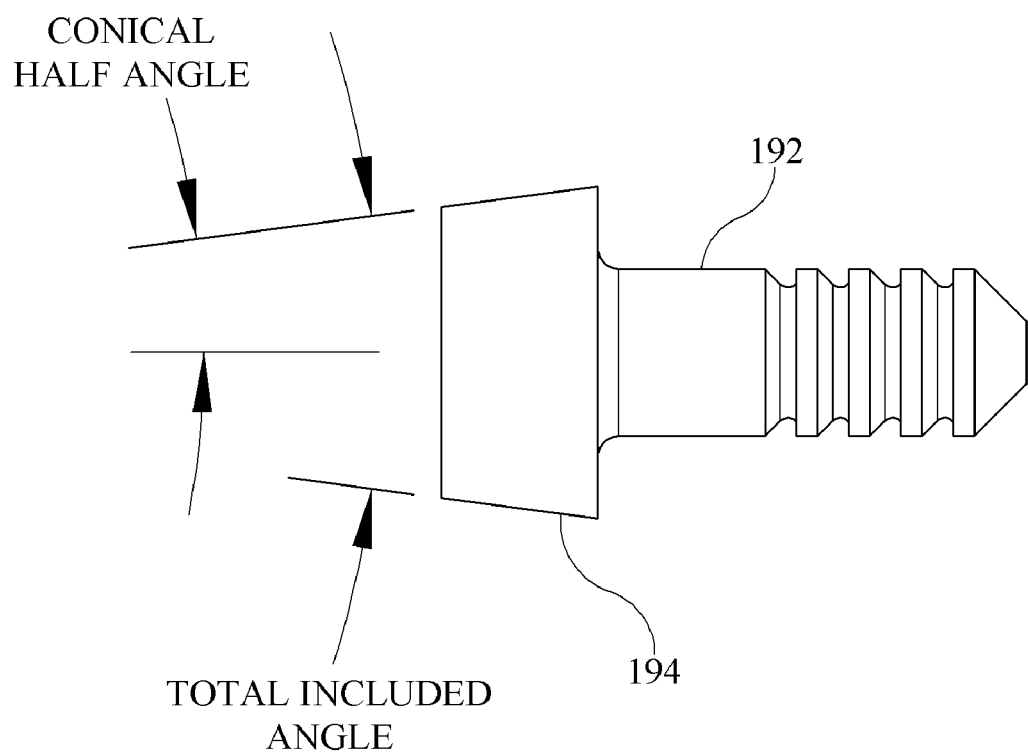

FIG. 8b is a side view of the same post.

Figure 9A:
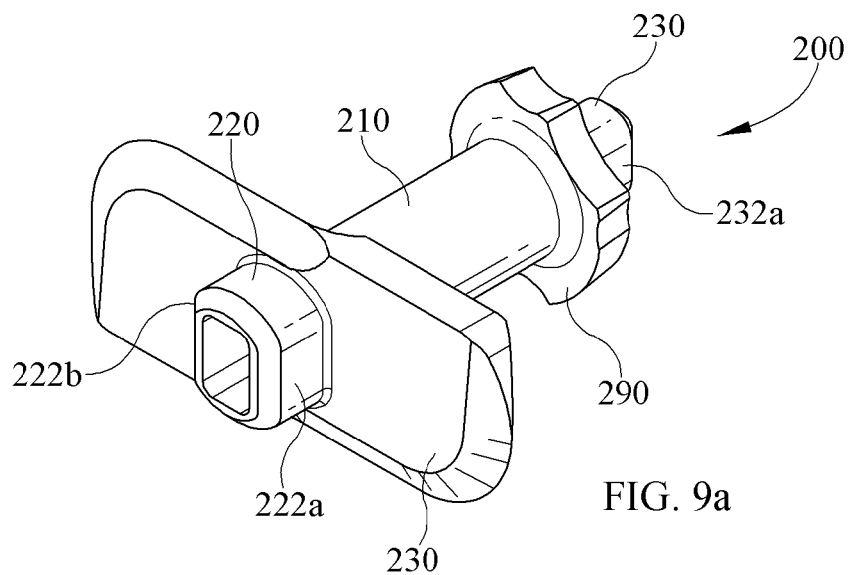
Figure 9B:
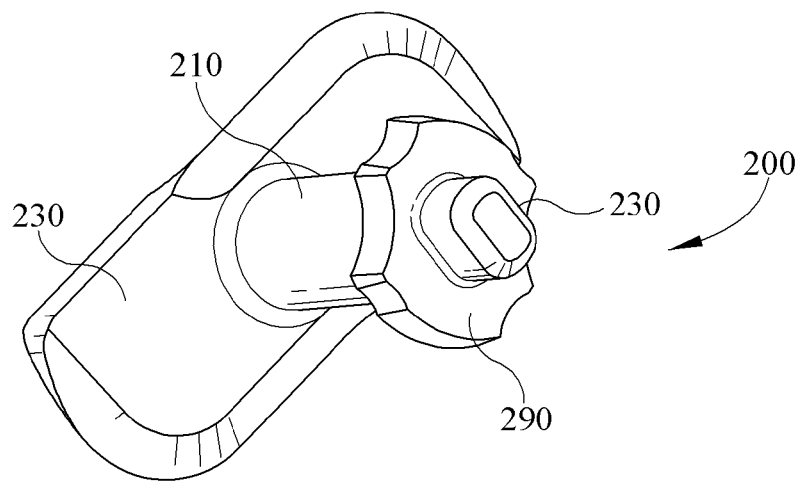
Figure 9C:
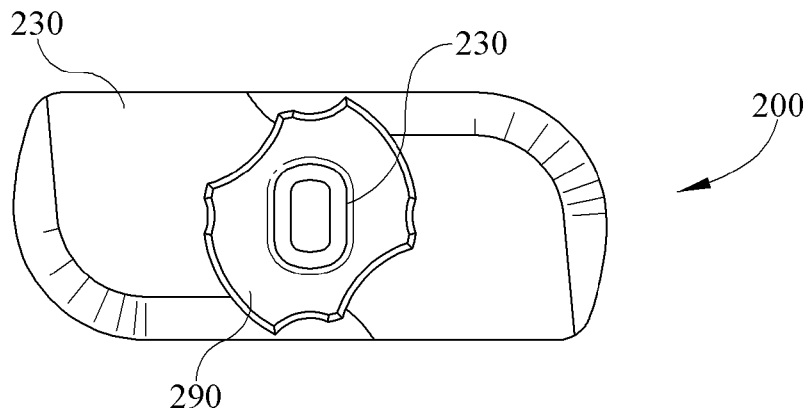

FIG. 9a is a three-dimensional illustration of the spin-plate. FIG. 9b is a three-dimensional illustration of the spin-plate from another perspective. FIG. 9c is an end view of the spin-plate.

Figure 10A:
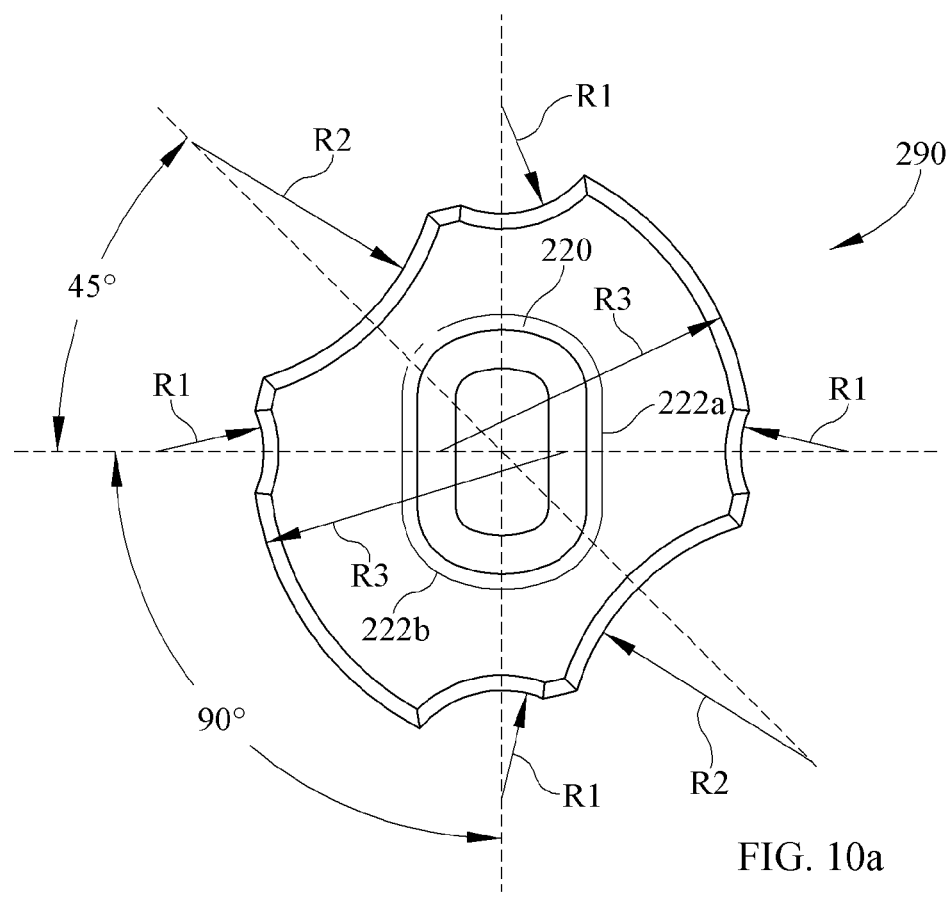
Figure 10B:
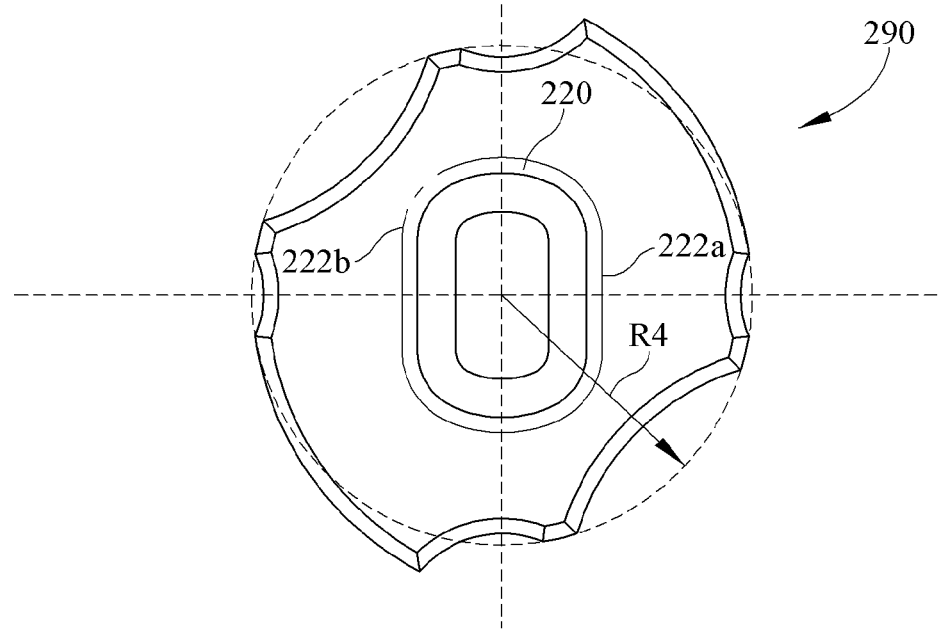

FIG. 10a and FIG. 10b illustrate details of the shape of the disc.

Figure 11:
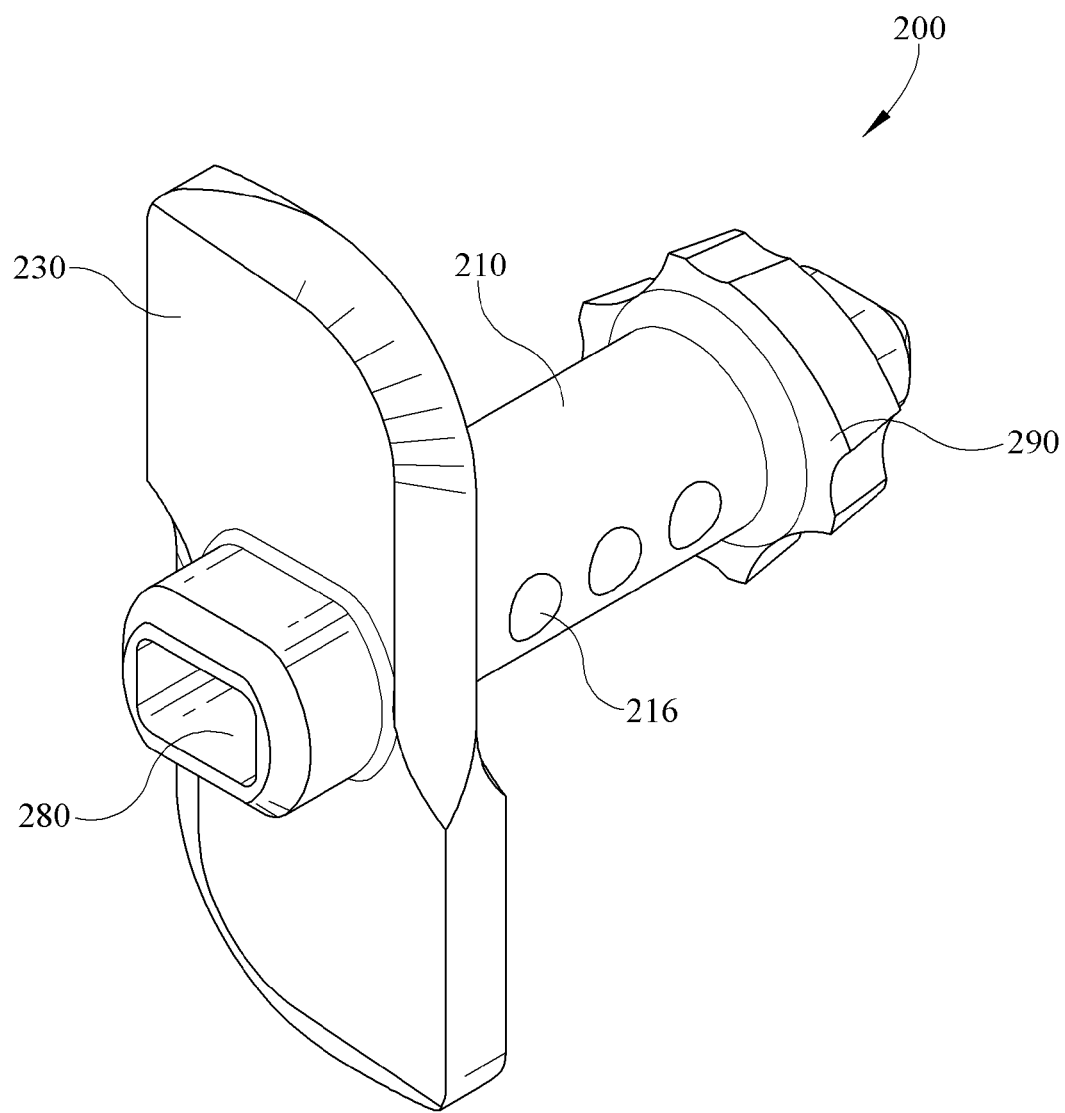

FIG. 11 is a three-dimensional view of a spin-plate having optional fenestration openings.

Figure 12:
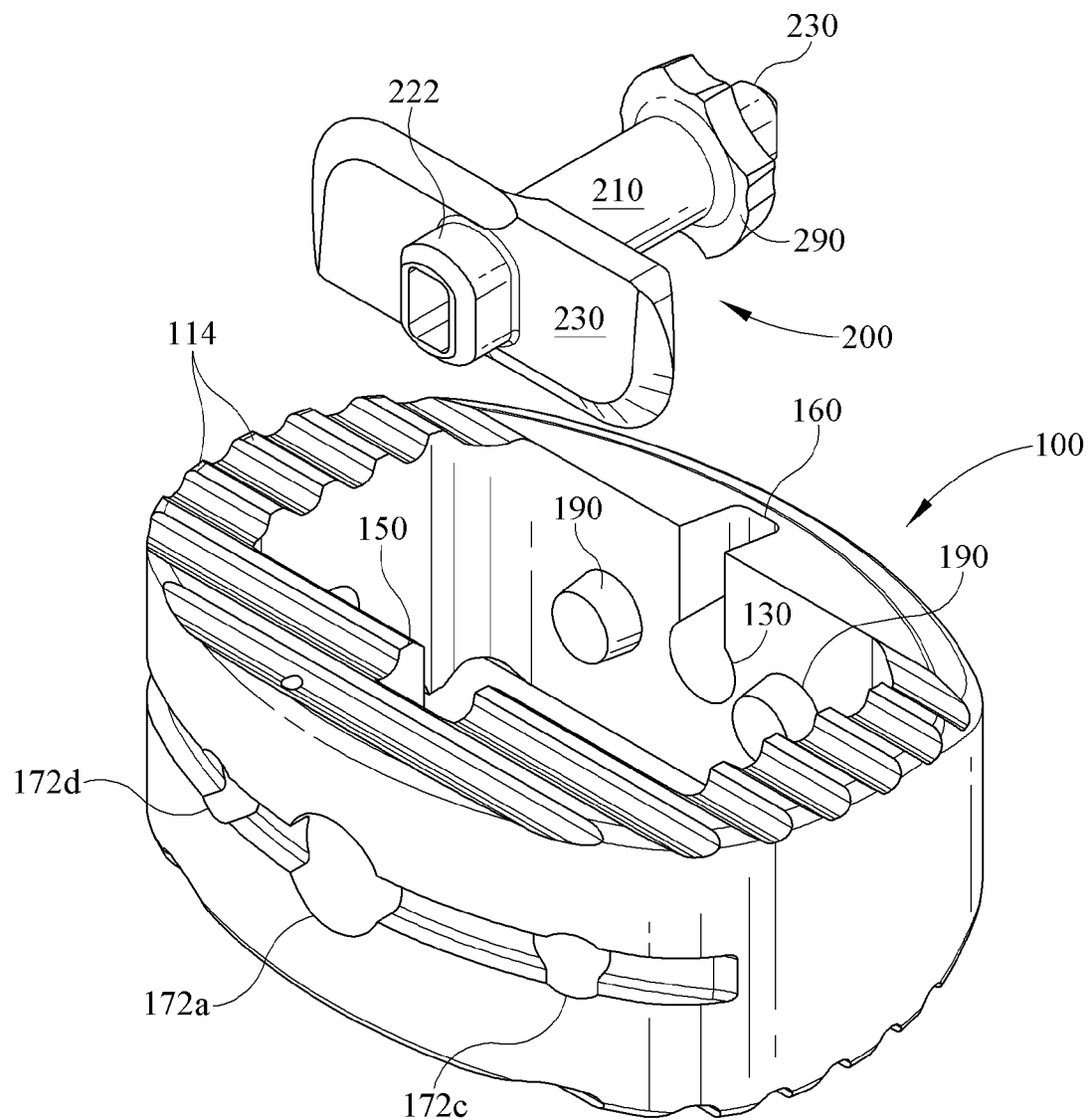

FIG. 12 is a three-dimensional view of the spin-plate in a position in that it is about to be installed into the spinal cage.

Figure 13A:
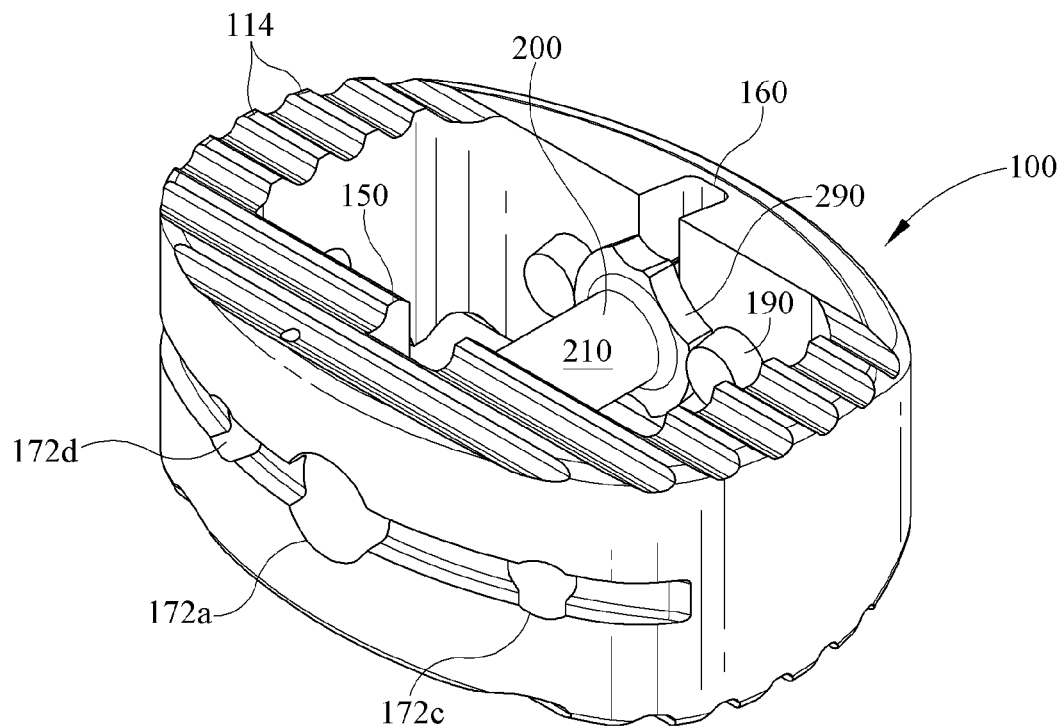
Figure 13B:
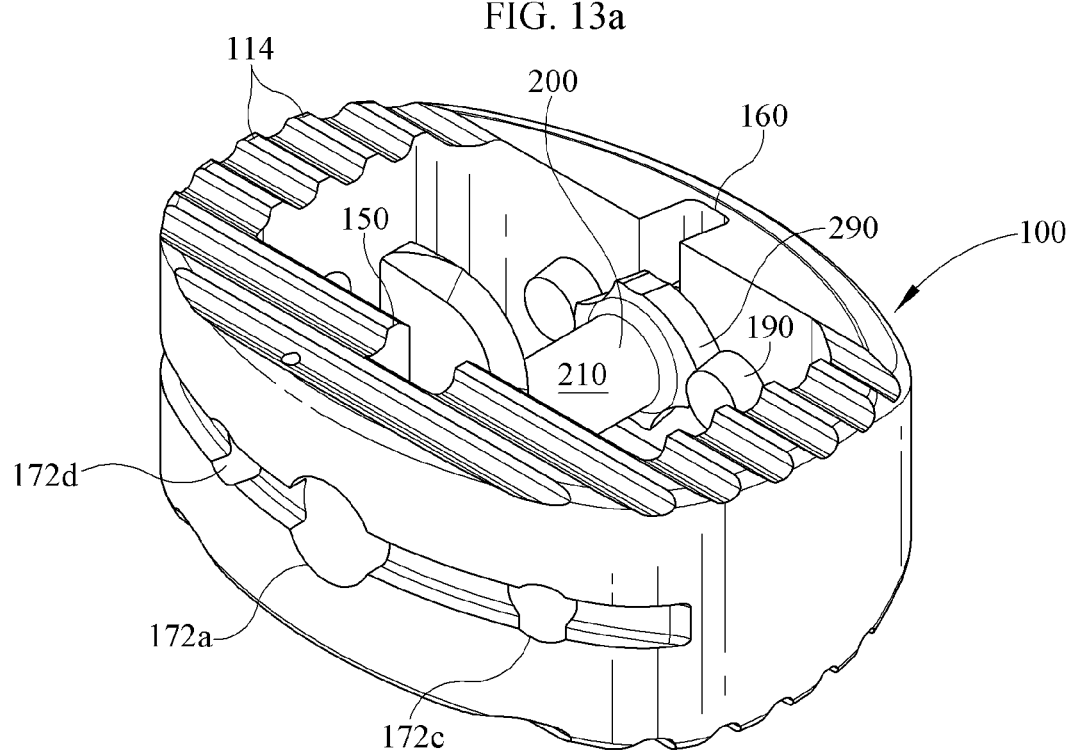

FIG. 13a is a three-dimensional view of the assembled spinal cage and spin-plate, with the spin-plate in the neutral position. FIG. 13b is a three-dimensional view of the assembled spinal cage and spin-plate, with the spin-plate in the engaged position.

Figure 14A:
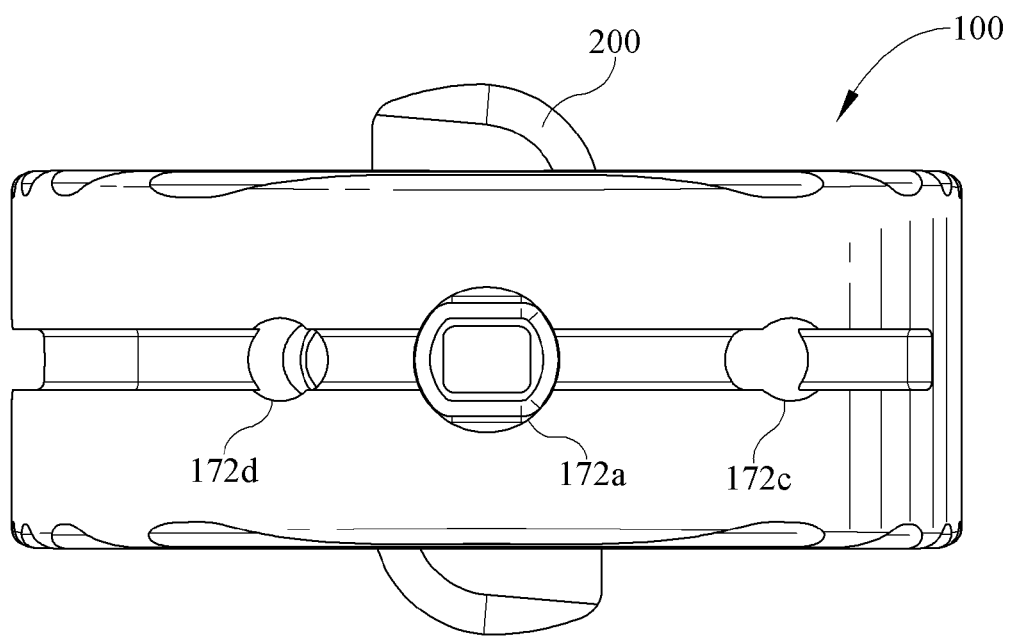
Figure 14B:
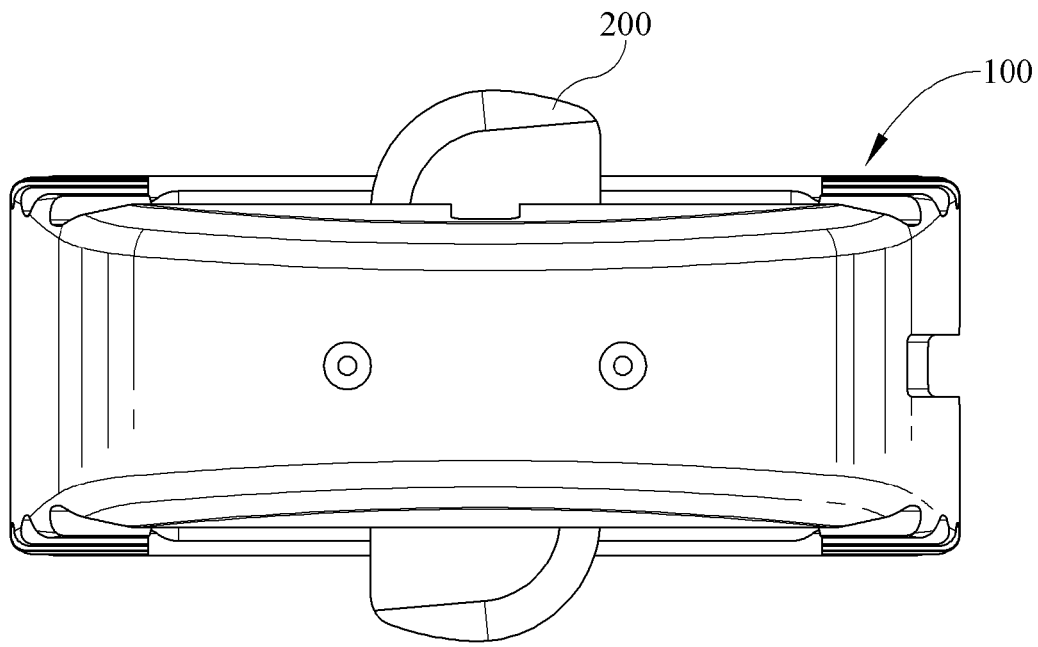

FIG. 14a is a front view of the assembled spinal cage and spin-plate, with the spin-plate in the engaged position. FIG. 14b is a rear view of the assembled spinal cage and spin-plate, with the spin-plate in the engaged position.

Figure 15A:
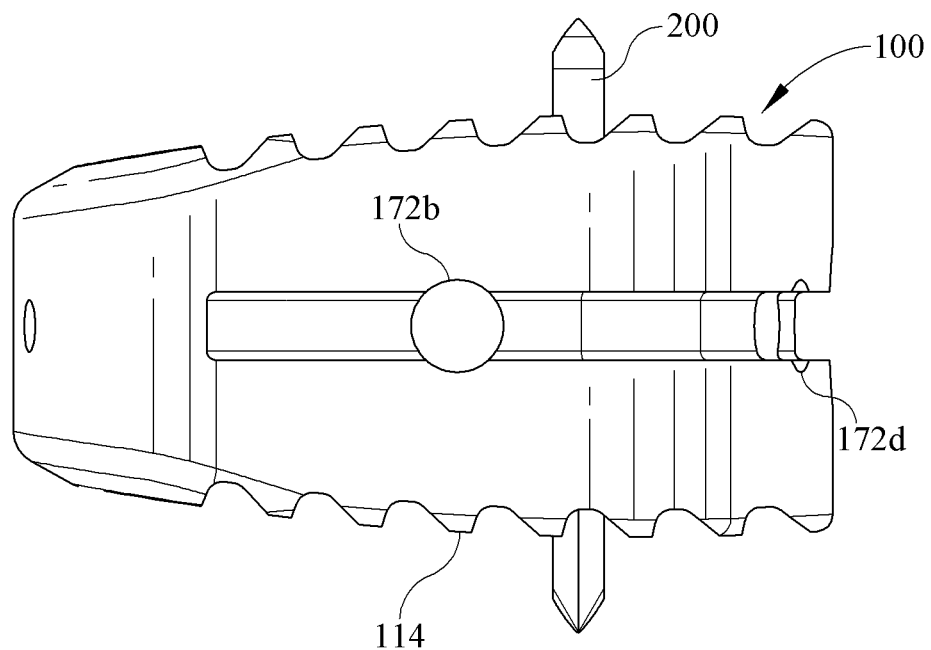
Figure 15B:
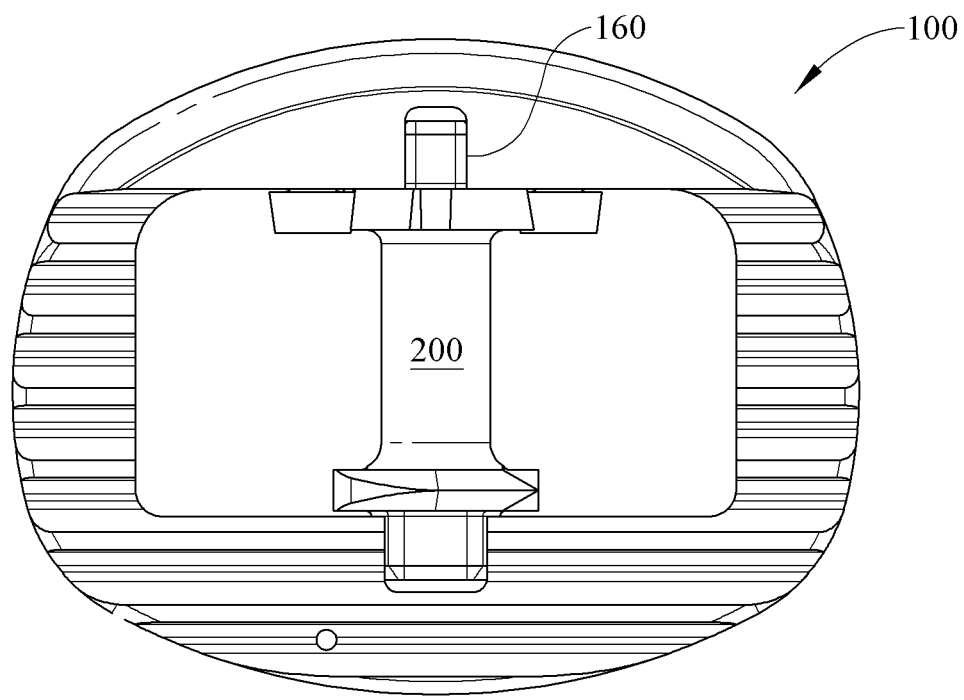

FIG. 15a is a side view of the assembled spinal cage and spin-plate, with the spin-plate in the engaged position. FIG. 15b is a top view of the assembled spinal cage and spin-plate, with the spin-plate in the engaged position.

Figure 16A:
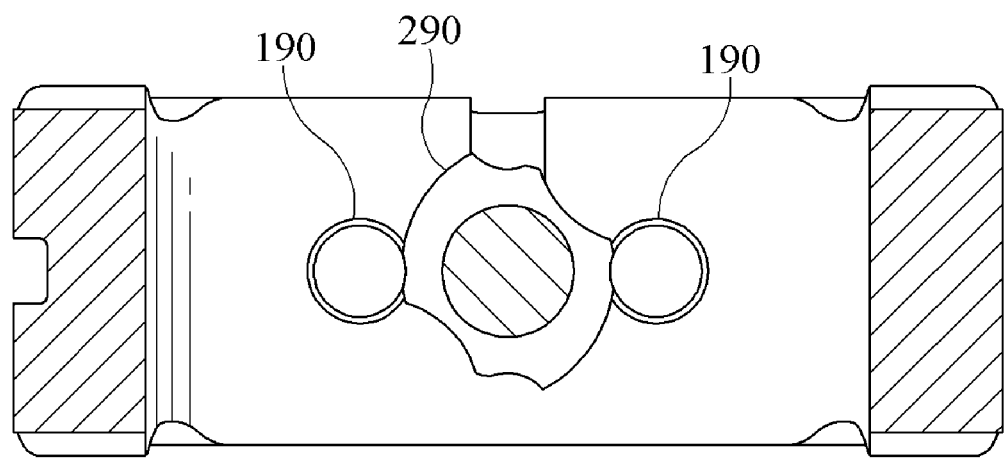
Figure 16B:
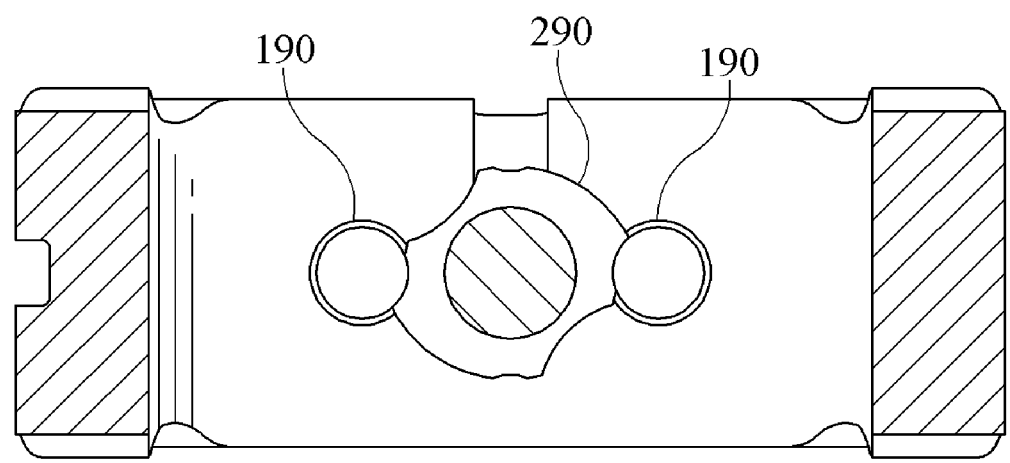

FIG. 16a is a view, looking along the shaft direction of the spin-plate, of the disc interacting with the posts in the neutral position. FIG. 16b is a view, looking along the shaft direction of the spin-plate, of the disc interacting with the posts in the engaged position.

Figure 17A:
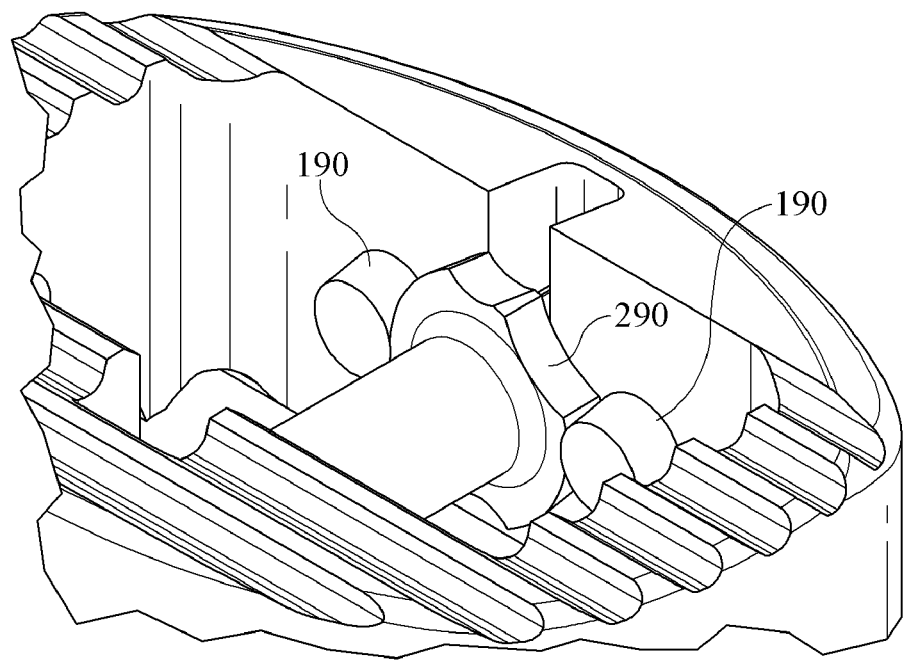
Figure 17B:
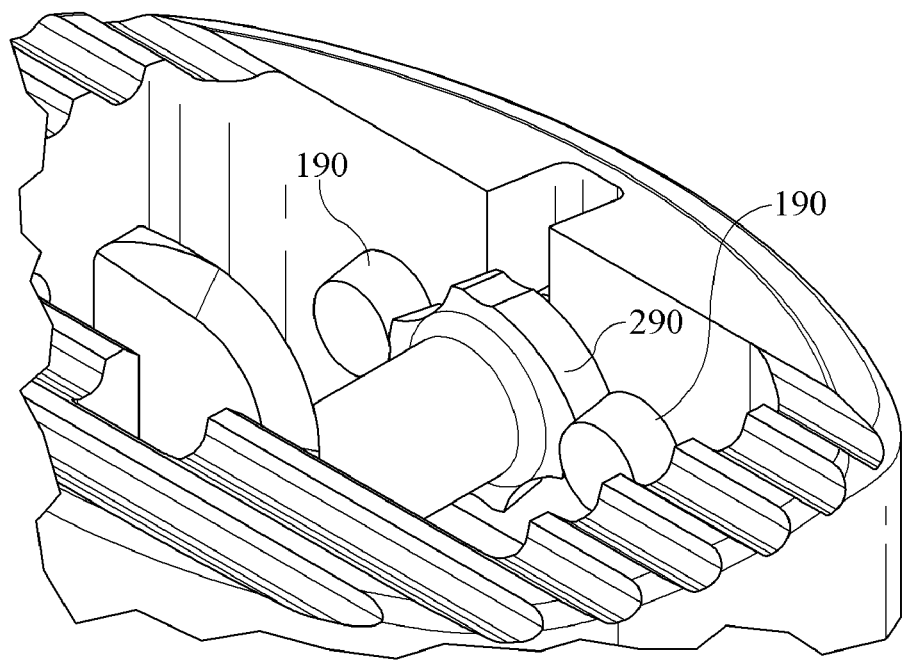

FIG. 17a is a localized three-dimensional view of the disc interacting with the posts in the neutral position. FIG. 17b is a localized three-dimensional view of the disc interacting with the posts in the engaged position.

Figure 18:
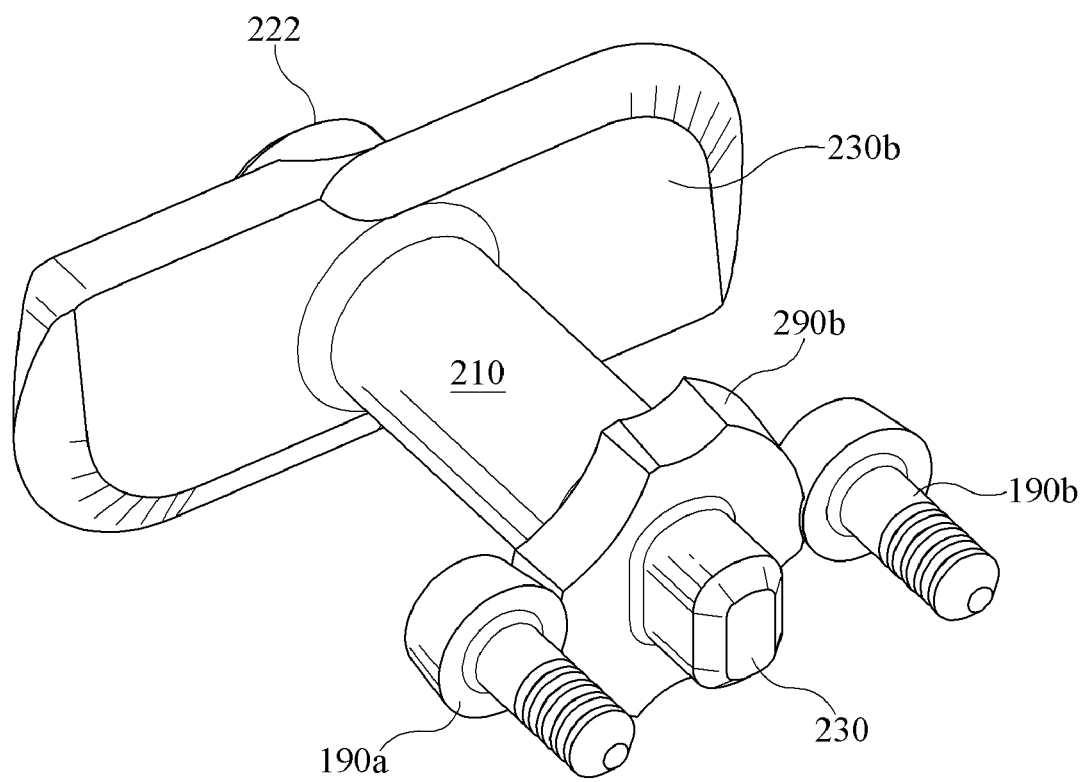

FIG. 18 is a three-dimensional view showing the disc interacting with the posts, in the neutral position. In this Figure, the spinal cage has been removed for clarity.

FIGS. 19a-19d show interactions between the disc and the posts for a slightly different contour of the disc.

Figure 20:
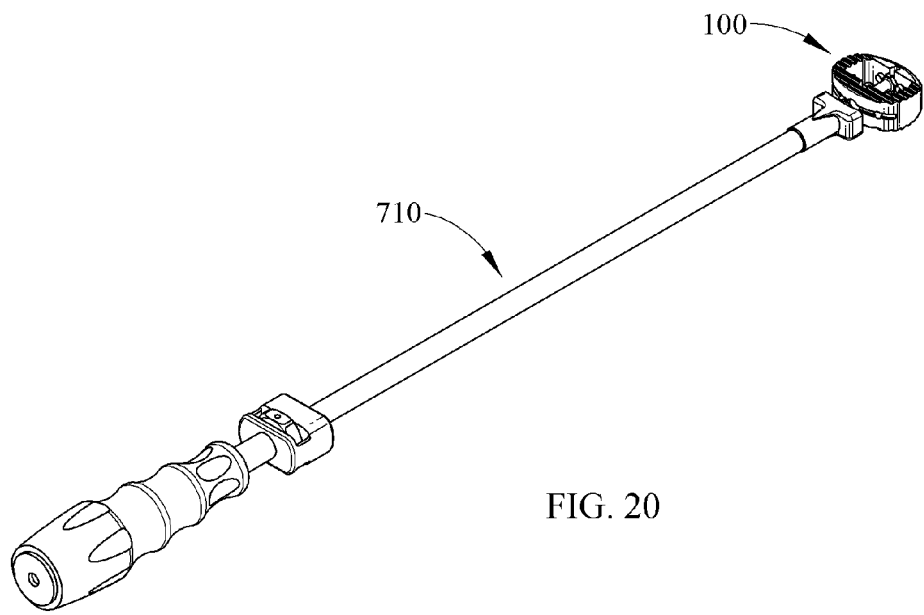

FIG. 20 shows an installation tool connected with a spinal cage assembly.

Figure 21:
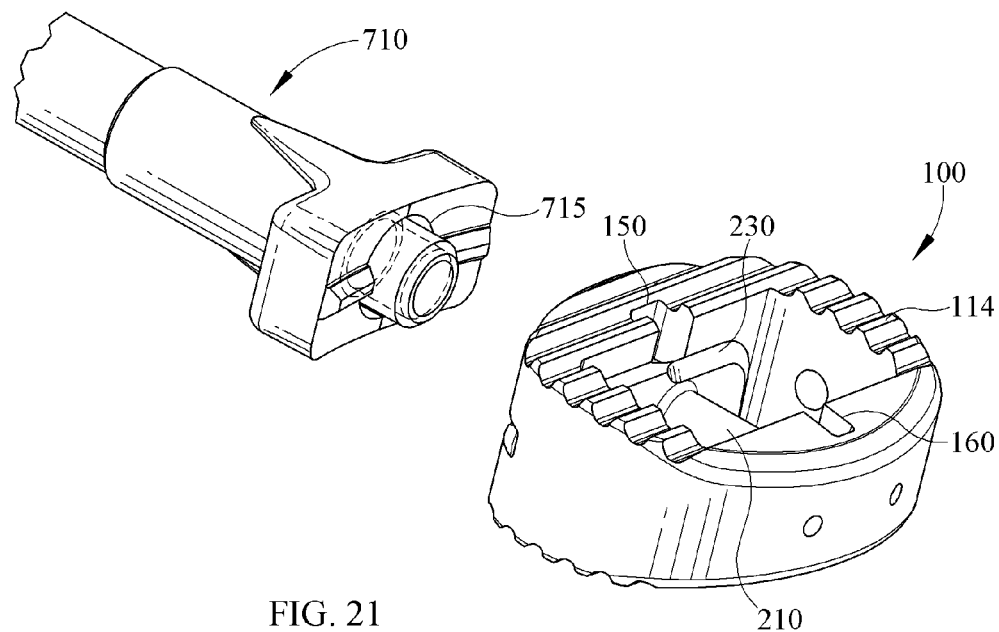

FIG. 21 is a three-dimensional view showing the tip of the installation tool ready to interact with the spinal cage assembly, in this case at the anterior face of the spinal cage assembly.

Figure 22A:
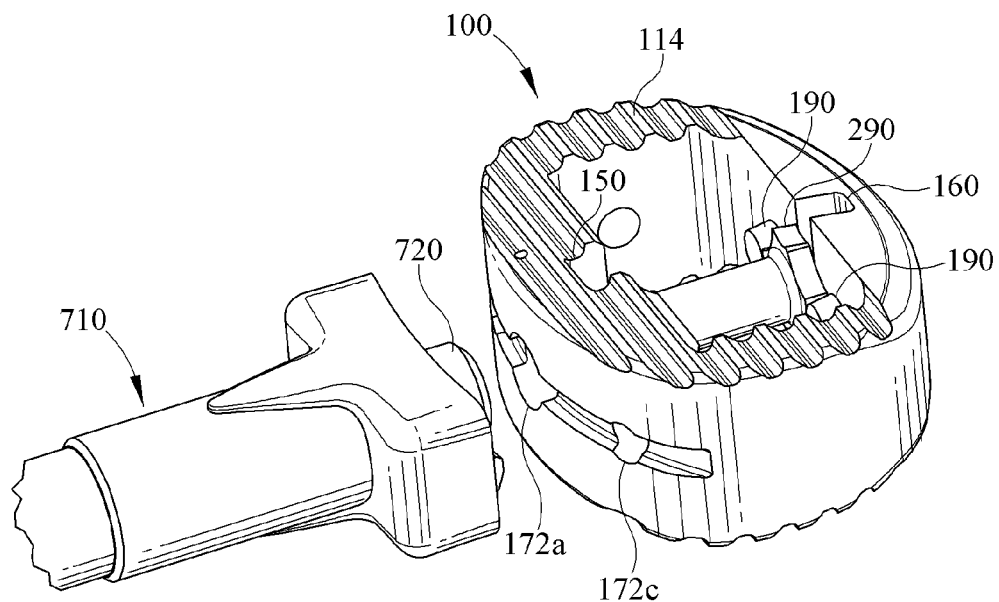
Figure 22B:
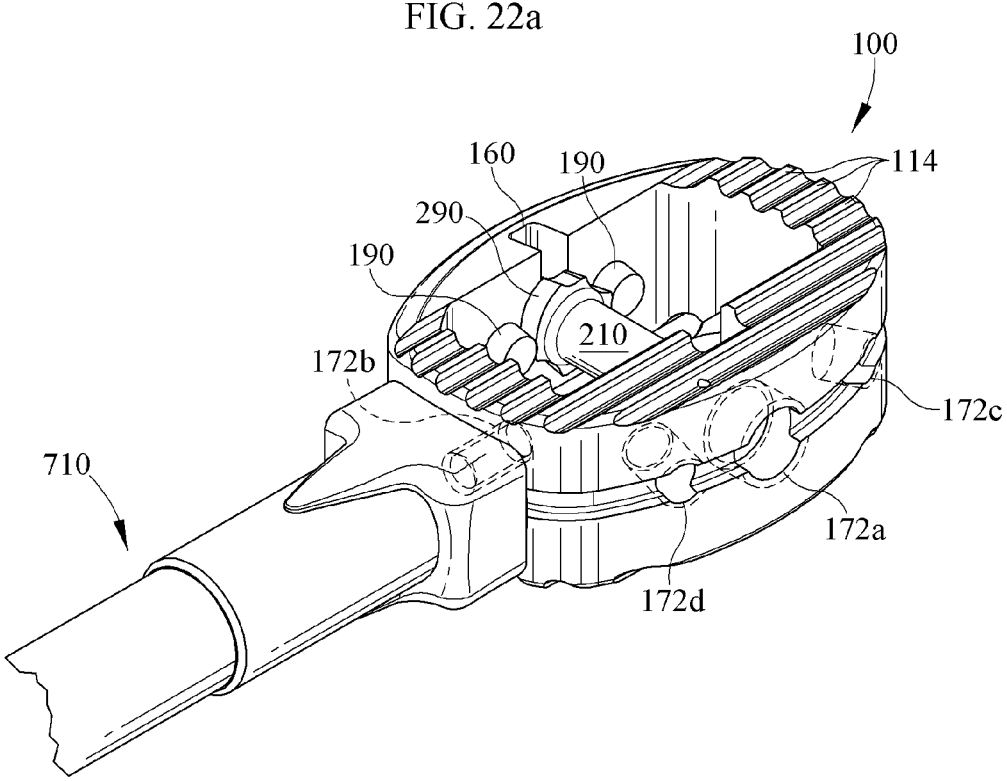
Figure 22C:
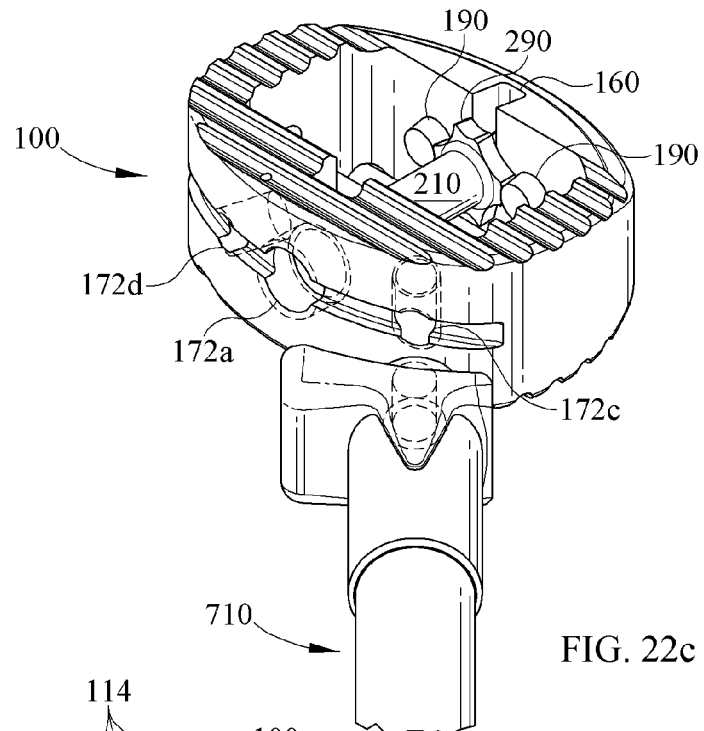
Figure 22D:
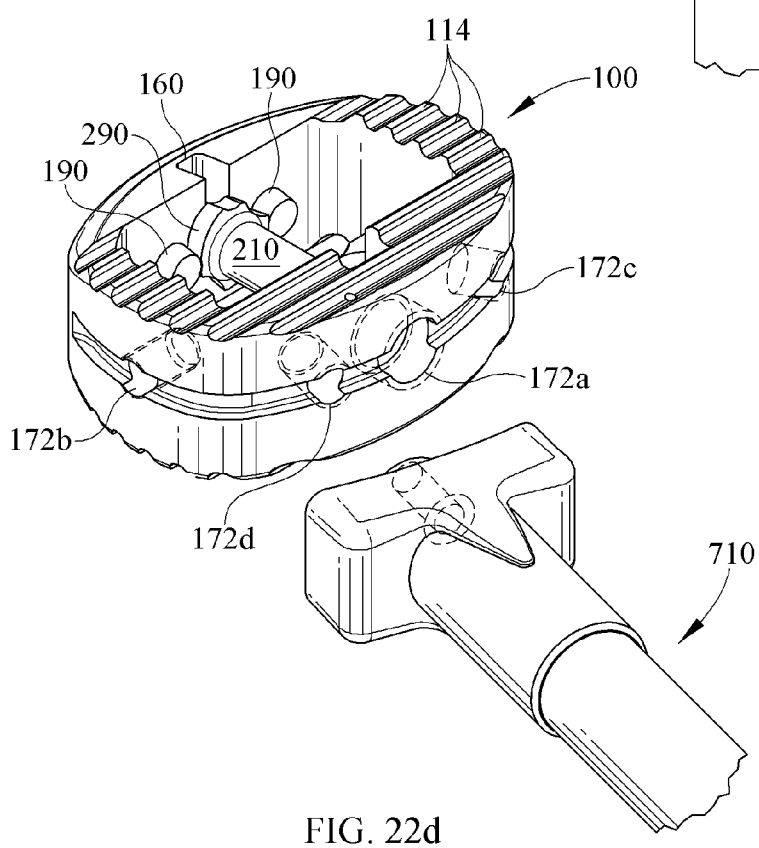

FIG. 22a is a three-dimensional view showing an installation tool almost connected to the spinal cage assembly for an anterior insertion. FIG. 22b is a three-dimensional view showing an installation tool connected to the spinal cage assembly for a lateral insertion. FIG. 22c is a three-dimensional view showing an installation tool almost connected to the spinal cage assembly for an anterolateral insertion at an orientation 45 degrees removed from anterior. FIG. 22d is a three-dimensional view showing an installation tool almost connected to the spinal cage assembly for an anterolateral insertion at an orientation 55 degrees removed from anterior.

Figure 23:
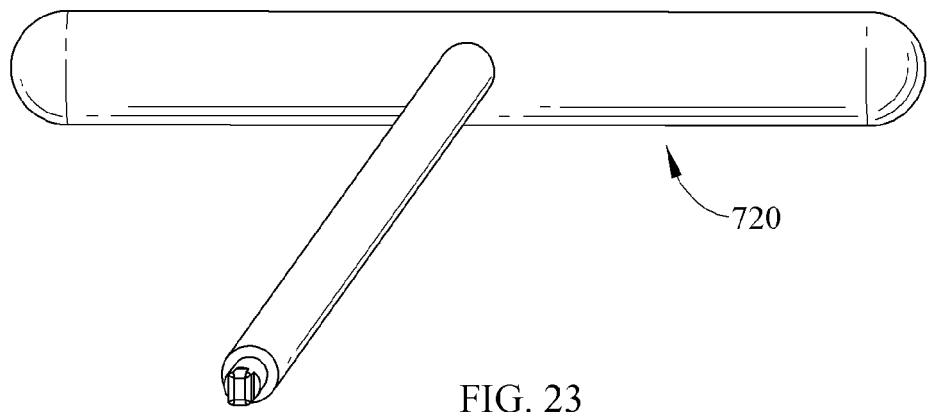

FIG. 23 is a three-dimensional view of a locker tool that can be inserted centrally in the installation tool for purposes of rotating the spin-plate.

Figure 24:
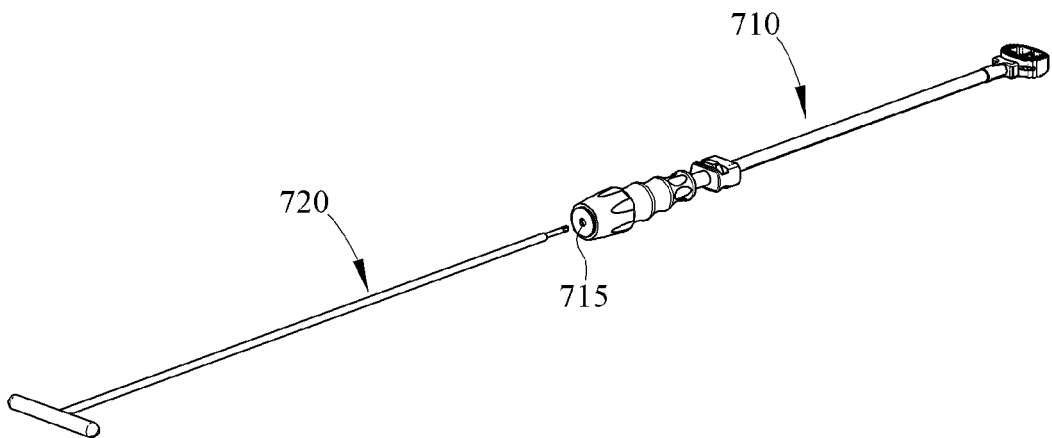

FIG. 24 is a three-dimensional view of the locker tool about to be inserted centrally in the installation tool for purposes of rotating the spin-plate.

Figure 25A:
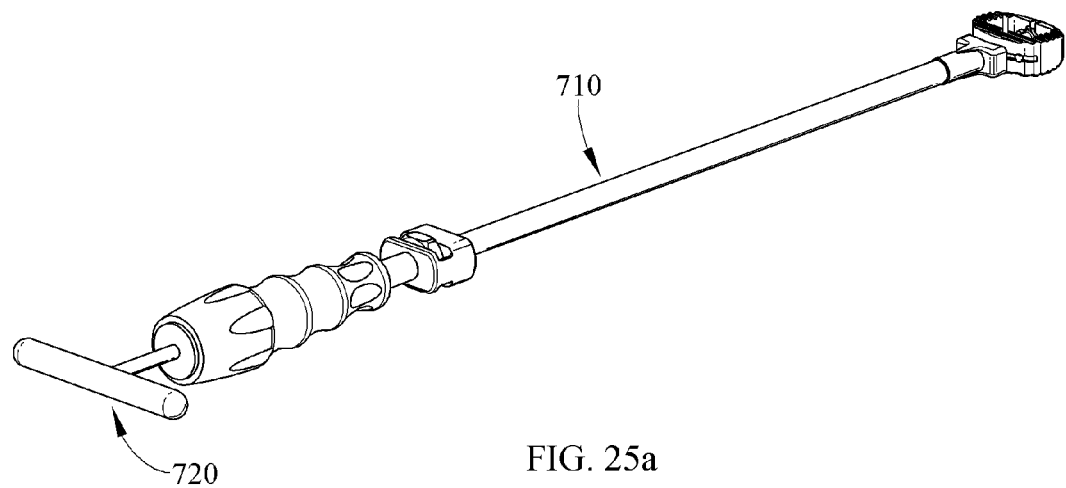
Figure 25B:
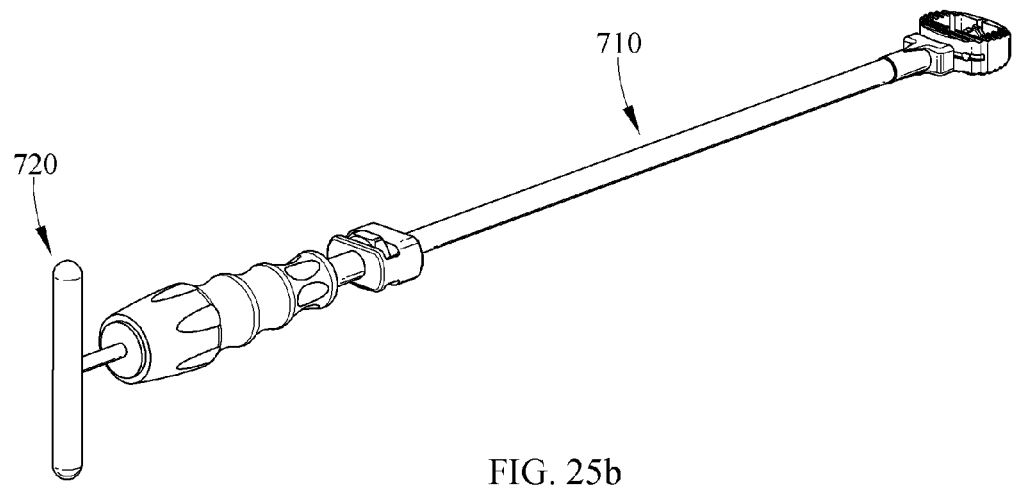

FIG. 25a is a three-dimensional view of the installation tool with the locker tool inserted in it, all connected to a spinal cage assembly, with the blade in the neutral position. FIG. 25b is a three-dimensional view of the installation tool with the locker tool inserted in it, all connected to a spinal cage assembly, with the blade in the engaged position.

Figure 26:
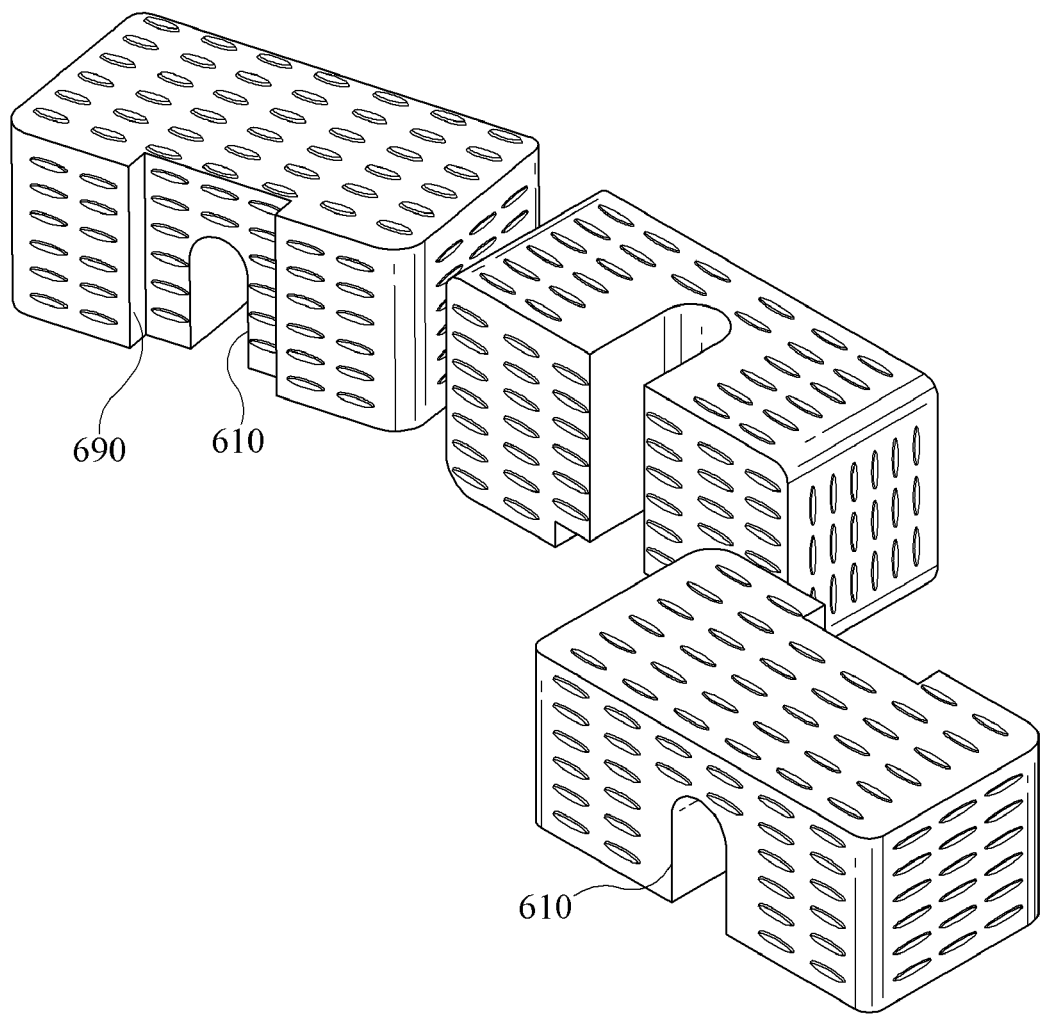

FIG. 26 is various three-dimensional views of a filler piece that might be placed in the empty space inside the spinal cage, when the spin-plate is present.

Figure 27:
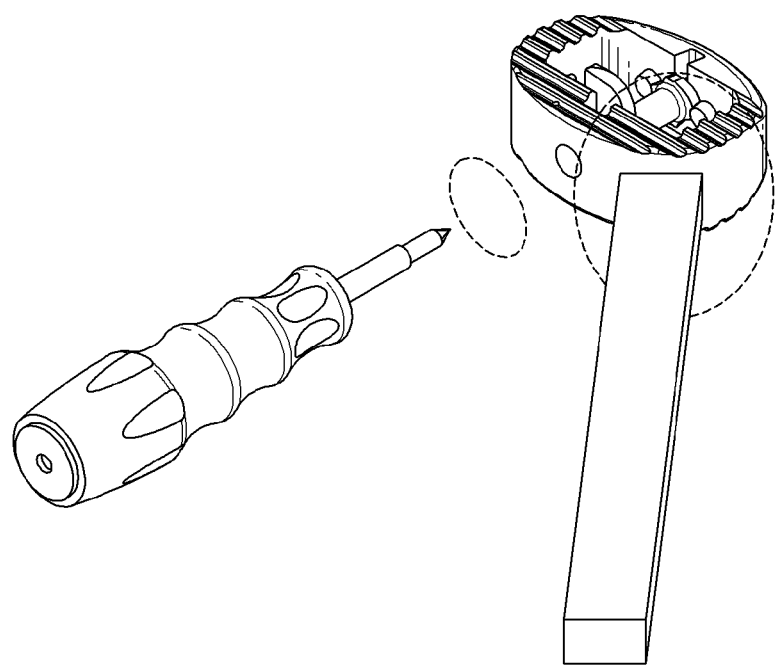

FIG. 27 illustrates a surgical procedure using one approach for introduction of the spinal cage assembly and another approach to cause rotation of a member of the spinal cage assembly.

Figure 28:
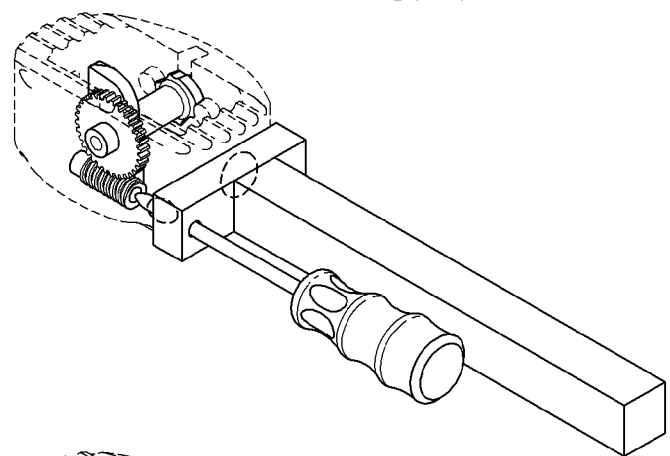
Figure 29:
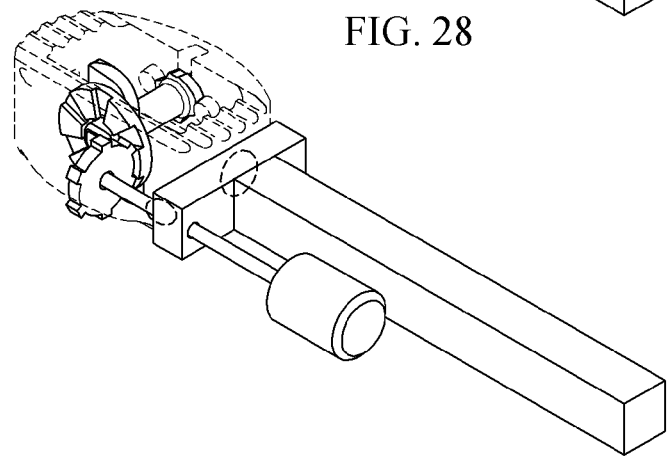

FIGS. 28 and 29 illustrate spinal cage assemblies that contain gears to re-orient rotational motion delivered to the spinal cage assembly by a tool.

DETAILED DESCRIPTION

An embodiment of the invention includes a spinal cage and a deployable member that can removably fit inside the spinal cage. The deployable member may be a spin-plate that is able to rotate in order to be deployed. The spinal cage may be implanted in a patient either with or without the deployable member.

Figure 1:
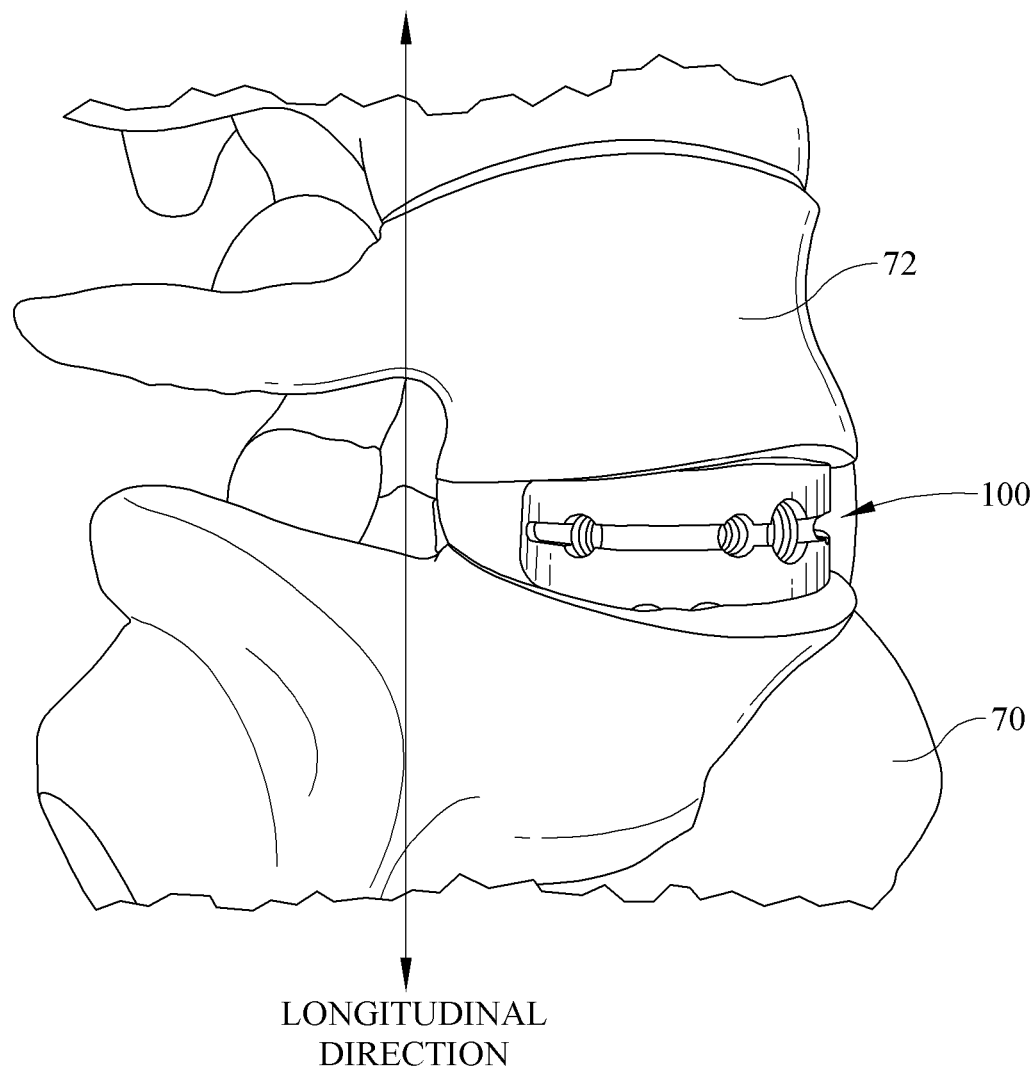
FIG. 1 is a three-dimensional view, showing an assembly of the invention in place between vertebrae of a patient's spine.

FIG. 1 illustrates a spinal cage assembly 10 placed between adjacent vertebrae 70 and 72. Spinal cage 100 is illustrated in FIGS. 2-8. Spinal cage 100 may have a longitudinal direction that extends generally from vertebra to vertebra 70, 72 in the installed situation. Spinal cage 100 may have a longitudinal dimension and related geometry that imposes the desired relative positioning between vertebrae 70 and 72 when the spinal cage 100 is in place in the patient. This positioning may include a lordosis angle, which is an angle indicating the extent of non-parallelism between planes enveloping the two ends of the spinal cage.

Figure 2:
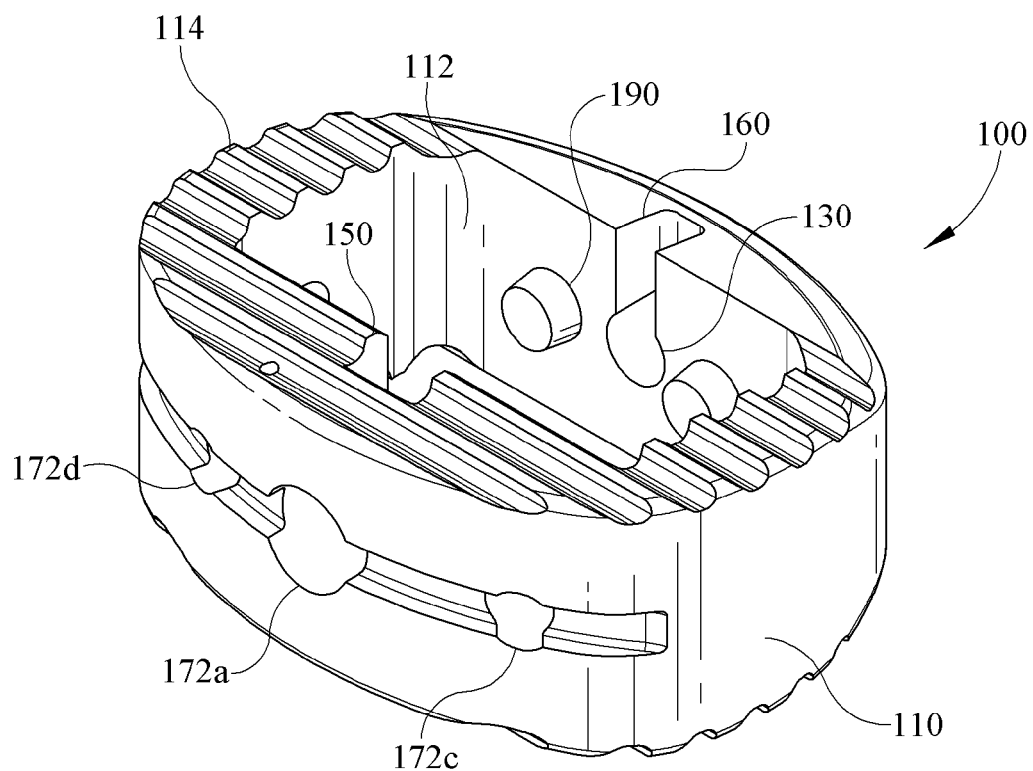
FIG. 2 is a three-dimensional illustration of a spinal cage.

Referring now to FIG. 2, spinal cage 100 may comprise a wall 110 extending in the longitudinal direction of the spinal cage 100 between vertebrae 70 and 72. In a plane approximately perpendicular to the longitudinal direction of the spinal cage 100, wall 110 may progress circumferentially in a closed curve that may at least approximately fit within an envelope of a vertebral cross-section. The closed curve of the wall 110 may define an interior space 112 inside wall 110. In the absence of a spin-plate as described elsewhere herein, the interior space 112 of spinal cage 100 may be substantially open space, available for the placement of materials conducive to bone ingrowth or for eventual bone ingrowth.

Figure 3:
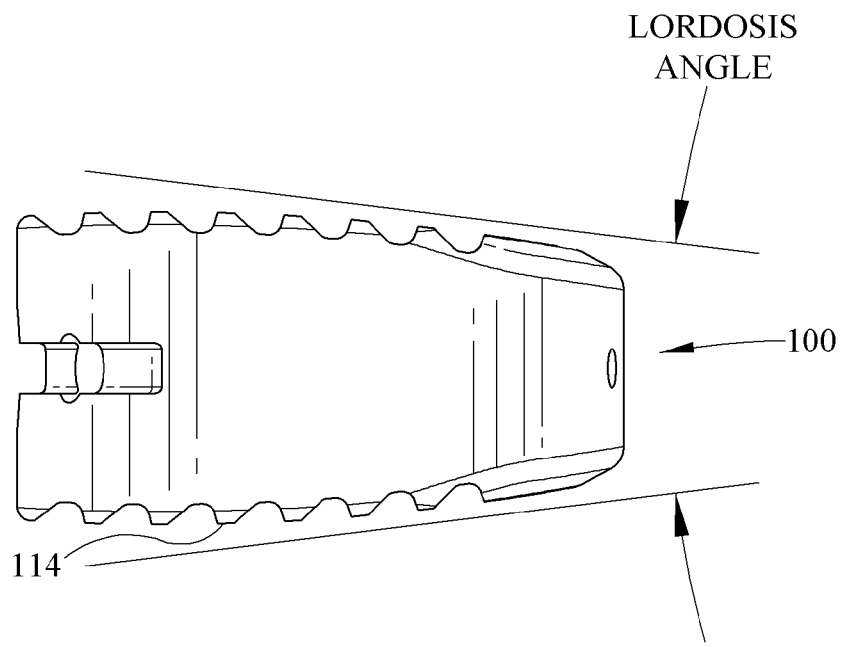
FIG. 3 is a side view of a spinal cage illustrating lordosis angle.
Figure 4A:
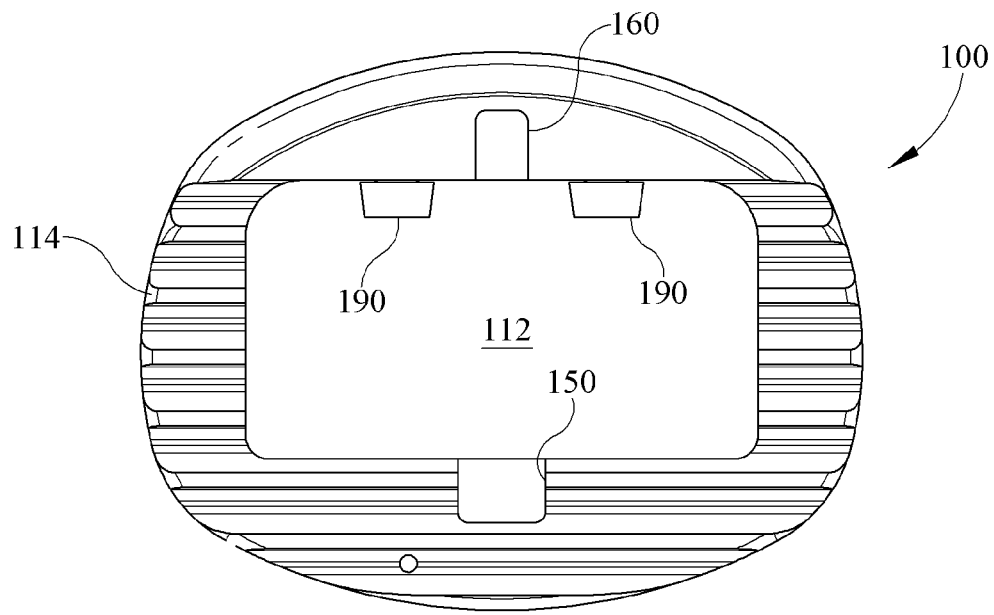
FIG. 4a is a top view of the spinal cage.
Figure 4B:
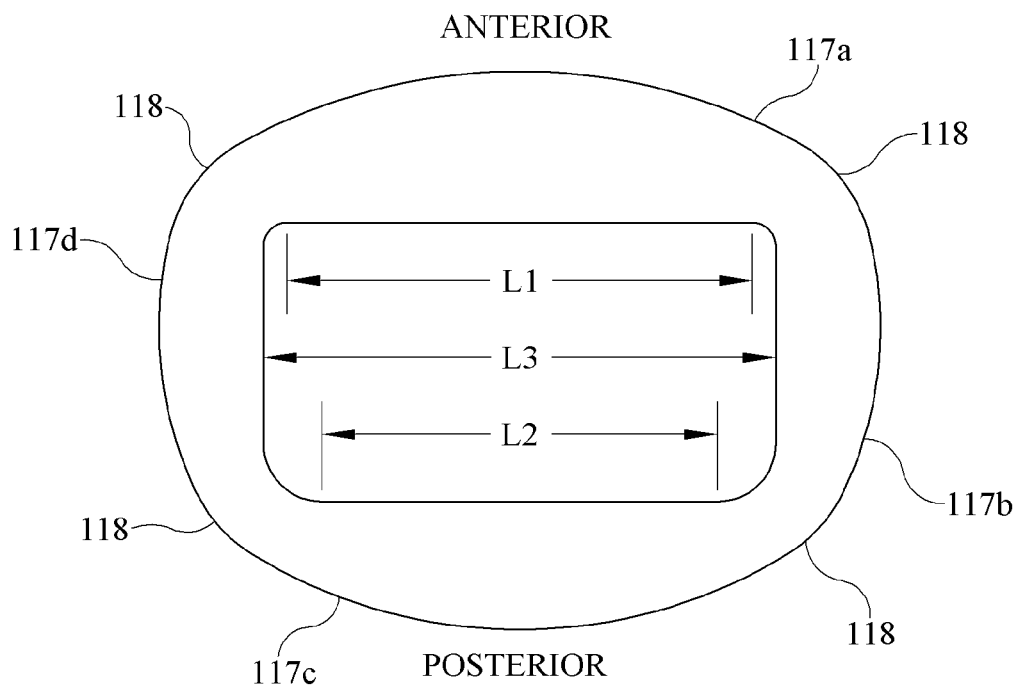
FIG. 4b is a cross-section of the spinal cage, in a plane perpendicular to the longitudinal direction of the spinal cage.

In some embodiments of the present invention, at least some features of the spinal cage 100 may be generally prismatic having a prismatic axis, which is the longitudinal axis of the spinal cage 100, and having a cross-section perpendicular to the prismatic axis. Along the prismatic axis, features of spinal cage 100 may generally be constant or repeated. The spinal cage 100 may have a height along the prismatic direction, but it is not necessary for either the external height of spinal cage 100 or the internal height of spinal cage 100 in the prismatic direction to be uniform everywhere. The spinal cage 100 may be wedge-shaped such that the two end faces 114 of spinal cage 100 are not parallel to each other, as described in connection with lordosis and as illustrated in FIG. 3. It is also possible that in localized places, some portions of spinal cage 100 may be missing or features may be cut into what would otherwise be a strictly prismatic shape. For example, it is possible for the end faces 114 of spinal cage 100 to have teeth or grooves or other local features that are not strictly prismatic. Referring to FIG. 4, a representative cross-section of spinal cage 100, taken perpendicular to the prismatic axis, is illustrated. This may be considered to be a cross-section of spinal cage 100 that does not encounter any special isolated features described elsewhere herein, such as openings, endplate features, or instrumentation interface features.

For spinal cage 100, a wall thickness of wall 110 may be defined as one traces a path around the internal perimeter. At each point on the internal perimeter, the wall thickness is defined by a distance to a nearest corresponding point on the outer perimeter of the spinal cage 100. The wall thickness as a function of position on the internal perimeter may be such that nowhere along the perimeter is there a constant wall thickness, but rather the wall thickness varies continuously as a function of position along the perimeter of the spinal cage 100.

The described cross-section of spinal cage 100 may have an external perimeter. The external perimeter may comprise four main curved segments 117a, 117b, 117c, 117d, and additionally may comprise corner radii 118 where the various main curved segments join other main curved segments, thereby comprising a total of eight curved segments connected in succession. Corner radii 118 can be identical to each other or different. Alternatively, the external perimeter of wall 110 may approximate an outline that somewhat resembles the shape of an intervertebral disc, such as, for example, the closed curve of the wall 110 may approximate a kidney-bean shape. Still other shapes of external perimeter are also possible.

The described cross-section of spinal cage 100 may have an internal perimeter. The interior perimeter may comprise at least two substantially straight-line segments, which may be opposed to each other and may be parallel to each other. The interior perimeter may comprise four substantially straight-line segments 119a, 119b, 119c, 119d at least some of which may be separated from other similar segments by rounded corner segments 119e. This is also illustrated in FIG. 4. Of these four substantially straight-line segments, two opposed substantially straight-line segments may have lengths substantially equal to each other. These two segments may be parallel with each other. The other two opposed segments may have lengths different from each other. These two opposed segments may be parallel with each other. In FIG. 4, the longer of these lengths is labeled L1 and the shorter of these lengths is labeled L2.

Between respective straight-line segments 119a, 119b, 119c, 119d, there may be internal curved corners having a radii of curvature that are either the same as each other or different from each other. The sharper internal radius of curvature may occur adjacent to the longer of the two substantially straight-line segments in an opposed pair. This may be of use for providing space for a spin-plate, as described elsewhere herein, having a blade that is as long as possible. A larger corner radius may be provided at other corners. This combination of features may provide maximum blade space near one extreme of the spinal cage 100 while providing improved local strength near an opposite extreme of spinal cage 100. It is appreciated that the internal perimeter may have substantially sharp corners or fewer than four straight-line segments.

The end faces 114 of spinal cage 100 may be roughened or have features appropriate to bite into the bone of adjacent vertebrae 70, 72. Grooves may be oriented so that it is relatively easy to insert the spinal cage 100 into an intervertebral disc space in the desired direction of insertion, and relatively more difficult to move the spinal cage 100 in the opposite direction. For example, the walls of the grooves may slope backwardly with respect to the intended direction of advancement. Although the illustration shows grooves that extend substantially laterally across a full width of the end surface of the spinal cage 100, this is not necessary. It is also possible to have teeth or still other geometries at end surfaces of spinal cage 100.

Figure 5:
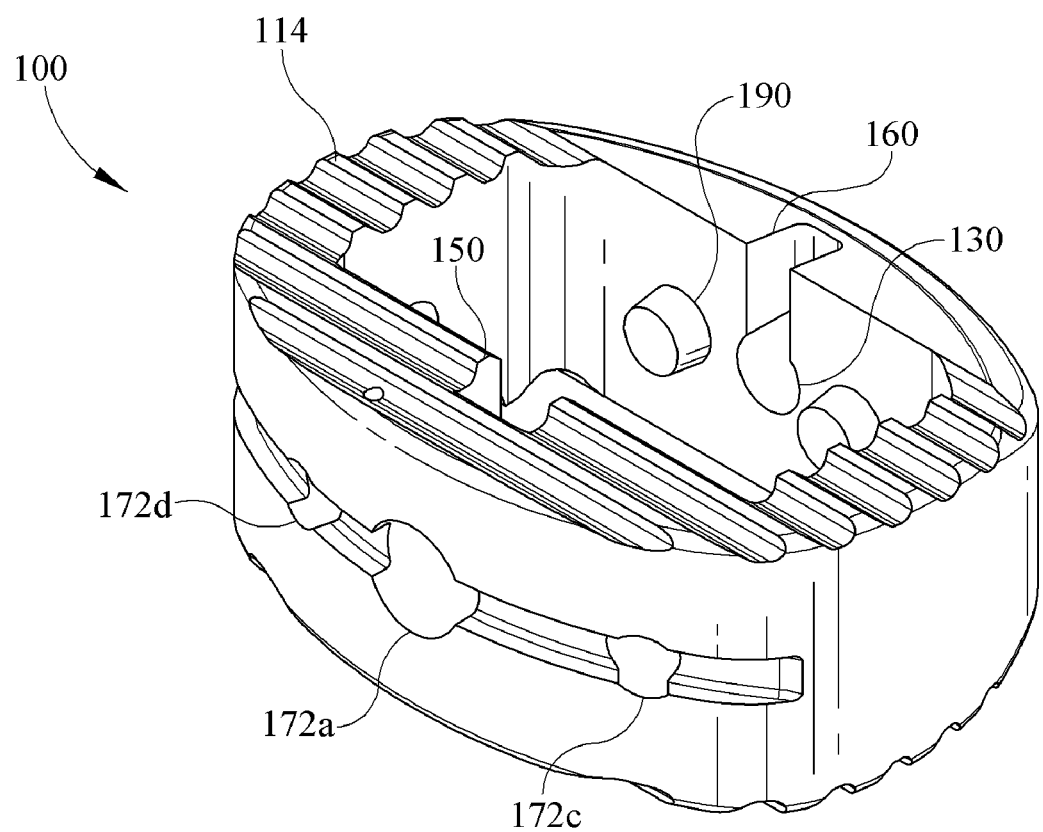
FIG. 5 is a three-dimensional view of the spinal cage describing groove details.

The wall 110 may comprise a flat plane on its interior surface that faces interior space 112. The flat plane may be substantially a laterally oriented plane, perpendicular to the anterior-posterior direction of the spinal cage 100. This is illustrated in FIG. 5. If the plane of that interior surface is projected laterally so as to intersect the entire spinal cage 100, that plane will divide the spinal cage 100 into a region that is posterior of the plane and a region that is anterior of the plane. It is possible that the region of wall 110 that is posterior of that plane may have, on its top and bottom surfaces, a tapered surface that is uninterrupted by grooves or teeth. The grooves or teeth may exist anteriorly of that plane.

Referring now to FIG. 7, spinal cage 100 may comprise an opening 120 through the wall 110, with the opening 120 having an opening axis. Opening 120 may be a through-hole through the wall 110. Opening 120 may be located on a plane of symmetry of spinal cage 100, or at the intersection of two planes of symmetry. Opening 120 may be internally threaded for a portion of its length. Opening 120 may be of a diameter suitable to provide access for a rotational tool for rotating the spin-plate 200 as described elsewhere herein, or for any other desired purpose.

Spinal cage 100 may further comprise an opposed concave feature 130 located in a part of wall 110 that is opposed to the location of opening 120. Opening 120 and opposed concave feature 130 may be coaxial. Opposed concave feature 130 may have a center of symmetry (such as a line axis of symmetry or a point of symmetry) that is a center of symmetry for at least some features of opposed concave feature 130, and that center of symmetry may lie along the opening axis of opening 120.

Opposed concave feature 130 may comprise any one or more of a recess, or a shaft-receiving blind opening or a shaft-receiving through hole, in any combination. Opposed concave feature 130, or at least a portion thereof may be symmetric about the center of symmetry.

Alternative possibilities include the possibility that both opening 120 and opposed concave feature 130 could be through-holes, and that one or both of opening 120 and opposed concave feature 130 could be stepped openings or otherwise have a configuration more complicated than a simple cylindrical opening. As described elsewhere herein, it is possible that either or both of opening 120 and opposed concave feature 130, or a recess associated with either or both of 120, 130 might have a periphery that is not completely circular or is non-axisymmetric. Opening 120 and opposed concave feature 130 taken together may be suitable to define a position or an axis of a shaft of a spin-plate as described elsewhere herein.

A possible orientation is that opening 120 may be at the anterior of the spinal cage 100 and opposed concave feature 130 may be at the posterior of the spinal cage 100. Opening 120 may be adapted for use in interfacing with an installation tool, as described elsewhere herein.

The spinal cage 100 may have a groove 150 or two grooves 150, 160 that extend at least approximately in the longitudinal direction of the spinal cage 100. The groove or grooves 150, 160 may be on an interior-facing surface of the wall 110 of spinal cage 100. If there are two grooves 150, 160, the grooves 150, 160 may be located so that they substantially face each other. The groove(s) 150, 160 may extend from features 120, 130 all the way to one end of the spinal cage 100. If there are two grooves 150, 160, the grooves 150, 160 may be substantially parallel to each other and may extend in the same direction as each other. The grooves 150, 160 are shown as being straight although they do not have to be straight. In one embodiment, the grooves 150, 160 may be located such that their respective axes lie in a plane that is a plane of symmetry of the spinal cage 100.

It is possible that a groove 150, 160 may comprise an entrance region such as a tapered or curved entrance region 156 that may help the end of a component entering groove 150, 160 to find its appropriate place while accommodating inexact initial placement of the component with respect to groove 150, 160.

The two grooves 150, 160 may be identical to each other or they could be different from each other. For example, grooves 150, 160 may have respective groove widths that are different from each other. This may help to create a situation in which there is only one possible way for a spin-plate to be installed into the spinal cage 100. Such a situation may be desirable for preventing possible mistakes of assembly or procedure. Having grooves 150, 160 be different from each other may be appropriate to accommodate differences between the two ends of the spin-plate in terms of function or dimensions of the respective shaft ends, as discussed elsewhere herein.

Referring now to FIG. 6, the spinal cage 100 may comprise an installation tool interface for an insertion tool to connect to the spinal cage 100 during installation. The installation tool interface may define an insertion direction that may be at least approximately perpendicular to the local surface of the spinal cage 100 at the place where the insertion tool connects to the insertion tool interface. The insertion direction may be at least approximately parallel to the axis of the opening 120, which in turn may correspond to the axis of rotation of the spin-plate (described elsewhere herein) when the spin-plate is installed in the spinal cage 100.

This design could be used if the surgical approach for placement of the spinal cage 100 is an anterior surgical approach. For such a situation, the axis of the opening 120 could lie in a plane of symmetry of the spinal cage 100.

It is also possible that the spinal cage 100 could be designed for use with surgical approaches other than a straight anterior approach. For example, the spinal cage 100 could be designed for use with a lateral surgical approach. Still other surgical approaches may be possible, with corresponding choices of locations of opening 172.

Figure 6A:
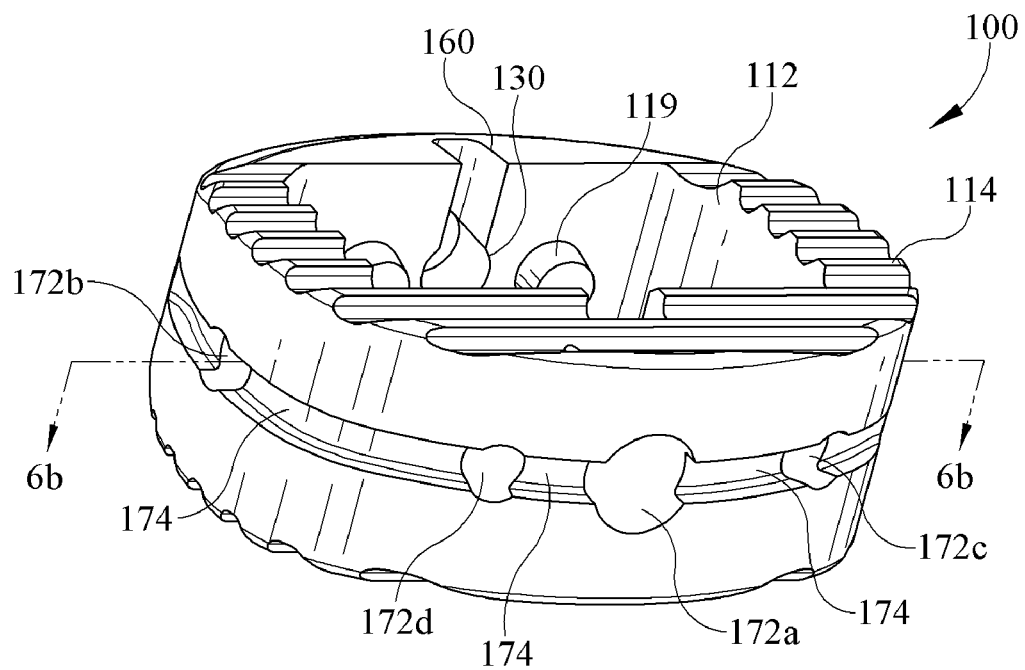
FIG. 6a is a three-dimensional illustration of a spinal cage illustrating features for interfacing with an installation tool.
Figure 6B:
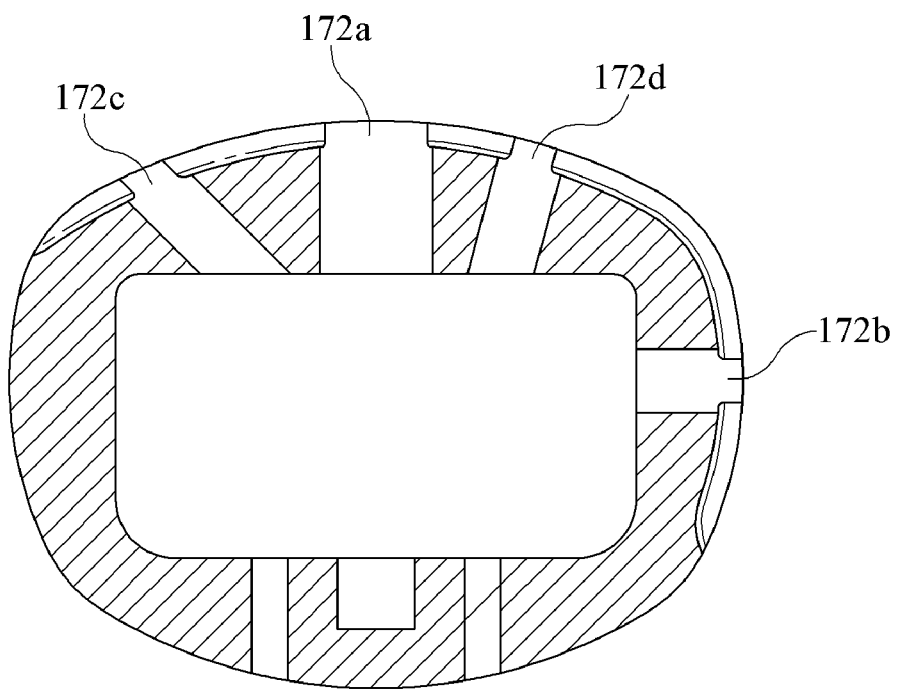

FIGS. 6a, 6b illustrate a spinal cage 100 that comprises interface features compatible with four different surgical approaches.

It is possible that the spinal cage 100 may comprise a plurality of interface features 172, such as openings on an external surface of the spinal cage 100, with an interface feature 172 corresponding to each possible surgical approach. For example, there may be an interface feature, such as an opening 172a in the anterior surface of the spinal cage 100, for use with an anterior approach. There further may be an interface feature, such as an opening 172b in the lateral surface of spinal cage 100, for use with a lateral approach. Interface feature 172b may be located approximately 90 degrees away from opening 172a, as viewed in FIG. 6. Still further, for use with an anterolateral approach, there may be an opening 172c through the external surface of the spinal cage 100 oriented at approximately 45 degrees away from the anterior direction. It is still further possible that an instrumentation interface may be provided for insertion of the spinal cage 100 from a direction that is closer to anterior than it is to any other direction, but is still somewhat removed from anterior. For example, the direction may be oriented approximately 15 degrees removed from anterior. In such a structure, there may be provided an opening 172d whose axis is oriented approximately 15 degrees removed from anterior. In the same structure, the opening 172d may be translationally offset from a true 15 degree opening pointing at the center of the spinal cage 100, so as to avoid overlap with other features of spinal cage 100 with which overlap might occur without such offset. It is further possible that the 45 degree interface opening 172c and the 15 degree interface opening 172d may be provided on opposite sides of the anterior interface opening 172a, again to avoid overlap of such openings with each other.

In general, interface openings 172 may be internally threaded. It is further possible that an interface opening, such as 172a, may have interface features such as an internal thread. These threads may occupy only a portion of the depth of opening 120 that may be coaxial with 172a. Such threads may be on a more exterior portion of opening 172a. At the same time, opening 172a may comprise features that interface with a spin-plate as described elsewhere herein. Such features may be on a more interior portion of opening 172a. The portion of opening 172a that interfaces with the spin-plate may be free from threads. The threads on some of the interface openings 172 may be identical to the threads on some other interface openings 172. Alternatively, threads on some interface openings may be different from the threads on other interface openings. For example, threads on opening 172a, which is illustrated as being a multi-purpose opening, may be larger than threads on openings 172b, 172c, 172d, which are illustrated as serving only as instrumentation openings.

It is further possible that a groove 174 may be provided on the external surface of the spinal cage 100, extending so as to meet at least some or (as illustrated) all of these interface openings 172. The groove 174 may be located at least approximately on a plane of symmetry of spinal cage 100, such as the midplane of the spinal cage 100, such plane being perpendicular to the prismatic axis of the spinal cage 100. This groove 174 on the exterior surface may extend more than 90 degrees of angle progressing around the external perimeter of spinal cage 100, such as extending through at least approximately 135 degrees of circumference. The groove 174 may cooperate with a corresponding feature on an installation tool. For example, groove 174 may cooperate with a feature of an installation tool to serve an anti-rotation function.

Various different spinal cages 100 of different sizes may be designed so that at least some of them share the same installation tool interface. such as curvature of the spinal cage external surface near the tool interface, dimensions of the tool interface groove 174, dimensions of interface openings 172a, 172b, 172c, 172d, etc. In this way, an installation tool can interface with multiple size variations of spinal cages 100.

Dimensions of the spinal cage 100 or of various spinal cages in a set may include an overall height that ranges from 8 to 16 mm, footprint dimensions that range from 27 mm to 39 mm in width and 21 mm to 30 mm in depth, and lordosis angles that range from 8 degrees to 15 degrees. The set of spinal cage sizes may for example comprise a typical small size and a typical large size, with most patients being able to accept one or the other of those two sizes. There may further be provided an extremely large size and an extremely small size for patients needing those particular sizes. For each individual footprint size of a spinal cage, a variety of spinal cages may be provided having respective combinations of heights and lordosis angles.

Referring now to FIGS. 7 and 8, the spinal cage 100 may comprise one or more posts 190 that may protrude from the spinal cage wall 110 into the interior space 112 of the spinal cage 100.

There may be two posts 190*a*, 190*b* may be located 180 degrees apart from each other with respect to a rotation center. The rotation center may be the center of feature 130 or on the axis of opening 120.

A simple possible form of post 190 is a cylindrical post, part of which is embedded in wall 110, and part of which protrudes into the interior space 112 of spinal cage 100.

Alternatively, the post 190 may comprise a stem 192 and a head 194, with the head 194 being larger in a transverse direction than is the stem 192. The stem 192 and the head 194 may be substantially coaxial, although this is not necessary. It is possible that the entire post 190 may be axisymmetric, although this is not necessary.

The post 190 may be cylindrical where it engages the spinal cage 100, and it may be cylindrical with a larger diameter where it does not engage the spinal cage 100. The post 190 may protrude into interior region 112 of spinal cage 100 at the portion that does not engage the spinal cage. It is appreciated that shapes other than cylindrical are also possible for post 190.

The stem 192 may be capable of being embedded into the spinal cage. For example, the stem 192 may fit with a press fit or an interference-fit within an opening in the spinal cage wall 110. The stem 192 may further comprise barbs or similar features that may be oriented in such a direction that inserting the stem 192 into the spinal cage wall 110 is relatively easier than removing the stem 192 from the spinal cage 100. Alternatively, posts 190 could be molded into spinal cage 100. As still another alternative, it is also possible that the post could be integral with the wall 110 of spinal cage 100.

The head 194 of the post 190 may be frustoconical. If frustoconical, the head 194 may have a head taper angle as illustrated, with the head being larger nearest to the wall 110 and smaller away from wall 110. The taper angle of the frustoconical head 194 may be chosen for purposes of interaction with features of the spin-plate, as described elsewhere herein. For example, a possible angle of taper of the frustoconical head 194 is approximately 15 degrees total included angle (7.5 degrees conical half-angle). This angle may be chosen appropriately so that when spin-plate 200 is in place, the frustoconical angle of the head 194, and a corresponding angle near the edge of the disc 290 that interacts with post 190, combines to trap post 190 in position in wall 110. This structure makes it impossible for post 190 to migrate out of the wall opening in which it is inserted. It is also possible that the cooperating angles, as spin-plate 200 is rotated, may urge spin-plate 200 forward possibly making some elastic deformation of spinal cage 100 available to help the rotation slip past certain detents in the normal course of rotation.

It is possible that the wall 110 of spinal cage 100 can be deflectable within an elastic limit such that under certain circumstances, the shape of the closed curve of wall 110 becomes slightly different from what it is in an undeflected-condition. For example, wall 110 can be deflectable in an anterior-posterior direction such that the distance between the anterior and posterior portions of the wall 110 increases. The amount of deflection can be suitable for snapping a spin-plate into place or can be involved in rotating the spin-plate, both of which are described elsewhere herein.

As described elsewhere herein, the wall 110 may be generally straight along the prismatic direction, with the possible exception of local geometric features. The wall may be straight both interiorly and exteriorly. Alternatively, it is possible that the wall 110 of the spinal cage 100 may have an inner surface (facing interior space 112) that is concave along a longitudinal direction from a first end to a second end of the spinal cage 100. Such a concave inner surface may provide increased space for bone ingrowth or for placement of material for aiding the ingrowth of bone, as compared to a wall 110 whose inner surface is substantially straight or prismatic.

The spinal cage 100 may be chosen to have a desired radiopacity. For example, the spinal cage 100 may be made entirely or mostly of radiolucent material such as a polymer (for example, polyetheretherketone (PEEK)). If the spinal cage 100 is made of such a radiolucent material, the spinal cage 100 could additionally comprise radiopaque markers placed in it at desired locations having known dimensions, spacing or orientation for later use during radiography. For example, the radiopaque markers could be or could comprise tantalum. The radiopaque markers could be in the form of spheres, rods or other simple shapes. The radiopaque markers could be press-fitted into appropriate cavities in spinal cage 100. Alternatively, radiopaque markers could be molded into spinal cage 100. The radiopacity of the spinal cage 100 may be chosen in combination with the radiopacity of the spin-plate 200 to achieve a desired purpose.

Embodiments of the invention can include a spin-plate 200 or more generally a deployable member. Spin-plate 200 is illustrated by itself in FIGS. 9-11. The spin-plate 200 may comprise a shaft 210 and a blade 230. Blade 230 may, as illustrated, be a substantially planar element that may have some sharpened edges. The plane of blade 230 may be substantially perpendicular to the axis of shaft 210. The blade 230 and the shaft 210 may be sized to fit inside spinal cage 100 for certain rotational positions of spin-plate 200, and to extend beyond the envelope of spin-plate 200 for other rotational positions of spin plate 200.

The blade 230 may be integral with shaft 210. Alternatively, blade 230 may be made as a separate part from shaft 210 and may be connected to shaft 210 either temporarily or permanently. It is possible that if the shaft 210 and the blade 230 are not made integrally with each other, they might be made separately from each other in such a way that a surgeon would have the ability to select and assemble blade 230 and shaft 210 to each other as desired at around the time of surgery. There may be, as illustrated, only one blade 230. Alternatively, it is possible that the spin-plate 200 could comprise or could be used with more than one blade 230 simultaneously. If so, the various blades 230 either could be identical to each other or could differ from each other in their dimensions, materials or in any other feature. For example, the position of blade 230 on spin-plate 210 could be chosen so as to provide a desired position of the blade 230 with respect to anatomical features such as regions or types of bone within a vertebra. If the blade 230 is near the middle of the length of spin-plate 210, blade 230 when deployed is likely to interact with cancellous bone. If blade 230 is closer to and end of spin-plate 210, blade 230 when deployed is more likely to interact with cortical bone. The position of spin-plate 230 on shaft 210 also may affect how much spreading-apart of the vertebrae could be acceptable at the location of blade 230. This may be due to patient motion prior to bony fusion, which in turn could affect how much extension of the spin-plate 230 from the envelope of the spinal cage 100 may be needed in the deployed condition to assure continued contact between the blade 230 and the vertebrae 70, 72.

Blade 230 could have an edge, which is the leading edge for the intended direction of rotational advancement of the blade into bone that is sharpened but otherwise smooth and continuous, as illustrated in FIG. 9 and elsewhere. Alternatively, it is possible that the blade 230 could comprise serrations or a plurality of teeth on surfaces that face bone for an intended possible direction of rotation for advancing the blade 230 into the bone. Such serrations or teeth may help provide suitable properties for cutting into bone. It is possible that the blade 230 could comprise at least one opening through the blade 230 or at least one indentation from an edge of the blade 230. Such openings or indentations could provide shape irregularities that newly formed bone can grow through or into or around, thereby helping to anchor the blade 230 in position in the patient after bone ingrowth has occurred. It is possible that the blade 230, in cross-section in a plane that includes an axis of rotation of the shaft 210, could comprise an undercut configuration. Such a configuration could also contribute to anchoring of the blade 230 and the spin-plate 200 generally into bone.

Various parts of the spin-plate 200 may have respective dimensions in directions that are radial or perpendicular to the axis of rotation of spin-plate 200. The shaft 210 may have a dimension such as a shaft diameter that is less than a corresponding maximum radial dimension of the blade 230.

Shaft 210 may comprise flats on the shaft on at least one end or both ends of the shaft 210.

An end of shaft 210 could have geometry as illustrated in FIG. 9 and elsewhere, comprising circular arcs and flats. The flats 222a, 222b and 232a, 232b may be parallel with each other. Flats at opposite ends of shaft 210 also may be parallel with each other. It is further possible that the end of shaft 210 could have still other geometries instead of the described circular arc and flats. It is possible that the end of the shaft may be non-axisymmetric. An end of shaft 210 may comprise a cross-section that is non-circular having, at various lines passing through the axis perpendicular to the axis, a smallest cross-dimension of the enlargement 250 and a largest cross-dimension of the enlargement 250. The orientation of the smallest cross-section dimension may be approximately perpendicular to the orientation of the largest cross-section dimension. As a result, the spin-plate 200 may be able to pass translationally longitudinally through groove 150, 160 for certain angular orientations of spin-plate 200 with respect to spinal cage 100, while being unable to pass through groove 150, 160 for other angular orientations.

The shaft 210 might comprise a rotational tool interface 280 suitable to transmit rotation from a tool to the spin-plate 200. Rotational tool interface 280 could be provided either at one end or at both ends of spin-plate 200. For example, if the spin-plate 200 can only be assembled into spinal cage 100 in one orientation, it may be that a rotational tool interface 280 for a rotational driving tool is not needed at both ends of shaft 210, but rather is only needed at one end. The shaft 210 may be designed accordingly.

The rotational tool interface 280 could be elongated such as a rectangle or rounded-rectangle. The long direction of the elongated tool interface could be parallel to the flats on the shaft 210 or flats on an enlargement of the shaft 210 at that end of the shaft 210.

A feature at one end of the shaft 210 may be different from a feature at the other end of the shaft 210. For example, the difference may be in a width of a flat at or near an end of the shaft 210, or more generally may be a smallest cross-section dimension of the enlargement 250. As described elsewhere herein, such a feature may have a function in determining whether a spin-plate 200 can be inserted into the spinal cage 100 in only one configuration or whether a spin-plate 200 can be inserted in two configurations by reversing the ends of the spin-plate 200. In some circumstances, it may be useful if the spin-plate 200 fits into the spinal cage 100 in only one configuration.

Referring now to FIG. 11, in some embodiments of the present invention, it is possible that the spin-plate shaft 210 may for at least for a portion of its length be hollow. For example, the shaft 210 may have a hollow interior 214 that is open at the end having tool interface feature 280, and that may be closed at the end opposite the open-ended end. Furthermore, communicating with the hollow interior 214 of the shaft 210, there may be fenestrations 216 that may be at least approximately transverse to the rotational axis of shaft 210. The fenestrations 216 may be at least approximately perpendicular to the rotational axis of shaft 210. The fenestrations 216 may be suitable to allow passage of bone-growth-promoting material or other liquid or semi-solid material. The end of the shaft 210, at which the hollow interior 214 is accessible, may be the end that is most accessible to the surgeon. Such as, for example, the end that has an interface 280 to accept tooling to cause rotation of the spin-plate 200. This end of the shaft 210 may further comprise a feature to interface with an injection device for injecting bone growth promoting material or other material into the shaft interior 214.

Fenestrations 216 through the side wall of the shaft 210 may exit the shaft 210 in such an orientation that, when the spin-plate 200 is in its final position in which the blade 230 is deployed to interact with adjacent vertebrae, the fenestrations 216 point laterally in the patient's body. Similarly, it is possible that the fenestrations 216 may point in an oblique direction, partly laterally but also having a component in the cephalad-caudal direction. In the illustration, spin-plate 200 is illustrated in its orientation in which the blade 230 is deployed to interact with adjacent vertebrae.

The spin-plate 200 may be designed to have a desired radiopacity for a specific purpose. The radiopacity of spin-plate 200 may be chosen in combination with the radiopacity of the spinal cage 100. Within the spin-plate 200 itself, the shaft 210 and the blade 230 could be made of the same material and may even be integral with each other. For example the entire spin-plate 200 could be made of metal such as a biocompatible titanium alloy. Alternatively, it is possible that the shaft 210 and the blade 230 could be made of different materials having different radiopacities. If less than the entire spin-plate 200 is radiopaque, then the components or features of the spin-plate 200 that are radiopaque could be placed having known dimensions or orientations or separation distances between the features or components. Dimensions or features of spin-plate 200 could be chosen for radiographic purposes. It is possible that some part of the spin-plate 200 could be more radiopaque than another part of the spin-plate 200. For example, the shaft 210 could be more radiopaque than a remaining part of the spin-plate, or the blade 230 could be more radiopaque than a remaining part of the spin-plate 200. If multiple blades 230 are present, individual blades 230 could have different radiopacities.

It is possible that the blade 230 of spin-plate 200, or any other part of spin-plate 200, may have a coating of a substance that is a member of the calcium phosphate family. For example, the coating may comprise hydroxyapatite or tricalcium phosphate. Such substances can be deposited onto a substrate, for example a metal substrate such as the blade 230 of spin-plate 200, by methods such as plasma spraying. Such coatings may promote the growth and interaction of bone with the component that they are deposited upon.

Some deployable parts may be resorbable. For example, the blade 230, or some portion thereof, may be resorbable. The blade 230 may, for example, comprise a resorbable polymer. If the blade 230 is resorbable, it is still possible that shaft 210 may be nonresorbable. Similarly, some portion of blade 230 may be nonresorbable.

The resorption time of the resorbable deployable part may be chosen so that the deployable part stays intact while bone growth is occurring and while there may be some risk of expulsion of the spinal cage. But, by the time resorption has completed, bone growth has occurred sufficiently to achieve fusion between the desired vertebrae. Use of a resorbable deployable part need not be limited to the described design involving spin-plate 200, but could be used as well with other designs of spinal fusion cages having deployable members that may be deployable by any form of motion.

The spin-plate blade 230 may be located so as to cut into cancellous bone in adjacent vertebrae rather than into cortical bone, because the cancellous bone might be easier to cut into. For example, if the spin-plate blade 230 comprises resorbable materials, the blade 230 might be less tough than would be the case for a metal blade, and so the blade 230 might be located so as to cut into cancellous bone. Spin-plate blade 230, if it is not itself radiopaque, may comprise a radiopaque marker.

Embodiments of the invention may include an assembly comprising the spinal cage 100 and the spin-plate 200. FIGS. 12-15 illustrate assemblies or features thereof. In general, the spin-plate 200 and the spinal cage 100 may be separable from each other. Spinal cage 100 may be suitable to be implanted in a patient either with or without spin-plate 200 as dictated by surgical needs.

It has been described elsewhere herein that the spinal cage 100 may have an internal perimeter whose shape is as illustrated in FIG. 4. The use of a sharper radius of curvature and the longer of the two unequal segments L1 compared to L2 may occur on the face nearest where the spin-plate blade 230 exists in the assembly. This may provide space for the blade 230 to rotate and may help to allow blade 230 to be as long as possible within geometric constraints of the overall spinal cage 100 and the assembly. When the spinal cage 100 is assembled with a corresponding spin-plate 200, the lateral dimension of the longer flat of the internal perimeter, labeled L1 in FIG. 4, may be at least as large as the largest end-to-end dimension of the blade 230 on the spin-plate 200. Alternatively, L3, which is the distance between the two opposed substantially straight-line segments, may be at least as large as the largest end-to-end dimension of the blade 230 on the spin-plate 200. This may be true for all cross-sections of spinal cage 100 or at least for a cross-section that passes through the rotational axis of spin-plate 200.

Various sizes of spinal cages 100 and various sizes of spin-plates 200 may be manufactured and may be provided to a surgeon in advance of surgery. The respective spinal cages 100 and spin-plates 200 may be such that various different spin-plates 200 can be inserted into a particular spinal cage 100, depending on the choice of the surgeon. The various different spin-plates 200 may differ from each other in some geometric feature. For example, the spin-plates 200 may differ in the respective lengths of their respective blades 230, so as to provide different depths of penetration of the blade 230 of spin-plate 200 into the bone of the adjacent vertebrae. The dimension L1 or alternatively the dimension L3 may be larger than the end-to-end dimension of the largest-bladed spin-plate that is contemplated to be used with a particular spinal cage 100. Of course, it is also possible to surgically implant a spinal cage 100 alone without the presence of any spin-plate 200. All of these decisions as to which spin-plate 200 to use with a particular spinal cage 100, or even whether to use any spin-plate 200 at all, can be made around the time of or during surgery.

The spin-plate 200 and the spinal cage 100 may be such that the spin-plate 200 can be engaged with or disengaged from the spinal cage 100 without the use of a tool. The engagement of the spin-plate 200 with the spinal cage may be able to be performed with a snap fit. It may also be possible to disengage the spin-plate 200 from the spinal cage by undoing the snap fit. Alternatively, a tool could be used to assist in insertion or disengagement. The engagement of the spin-plate 200 with the spinal cage 100 may be in such a way as to provide a positive indication that the spin-plate 200 has entered the spinal cage 100 and has reached the place where rotation of the spin-plate 200 can be performed. The positive indication can be tactile, such as a sharp change in the amount of force needed to advance the spin-plate 200 into the spinal cage 100, or audible, or both.

Engagement of the spin-plate 200 with the spinal cage may involve interaction at both ends of the spin-plate 200 with the wall 110. The spin-plate 200 may have a first end engaged with a first place on the wall 110 of the spinal cage and a second end engaged with a second place on the wall 110 of the spinal cage. The first place and second place may be substantially opposed to each other. It is possible that the first and second places may be on anterior and posterior portions of the wall 110 of the spinal cage, respectively. Other spin plate locations are also possible.

In general, it is possible that there is an initial angular position of the spin-plate 200 relative to the spinal cage 100, in which the blade 230 is contained within the spinal cage 100. That could be the configuration in which the assembly is moved into the patient's body. There can also be a final angular position of the spin-plate 200 relative to the spinal cage 100, in which the blade 230 extends beyond an envelope of the spinal cage 100. That could be the configuration at the completion of surgery. Blade 230 may have a maximum end-to-end dimension that is greater than the longitudinal dimension of the spinal cage 100 in at least some places in the spinal cage 100. This may ensure interaction of the blade 230 with bone when the blade 230 is in a deployed condition. Blade 230 may have a side-to-side dimension that may be measured in a direction approximately perpendicular to the direction in which the blade end-to-end dimension is measured. The blade 230 side-to-side dimension may be less than a longitudinal dimension of spinal cage 100 in at least some places in the spinal cage 100. This may ensure that when the blade 230 is in an undeployed condition, it does not interact with bone.

The spin-plate 200 may be designed so that the deployed angular position of the blade is 90 degrees removed from the undeployed angular position of the blade.

To go from the initial configuration to the final configuration, the spin-plate 200 may be capable of rotating 90 degrees away from the initial angular position in a specified direction of rotation. Embodiments illustrated herein permit 90 degrees of rotation in a specified direction of rotation, but more than 90 degrees of rotation is difficult or impossible, and rotation in the unintended direction of rotation is difficult or impossible. Alternatively, it is possible that rotation of the spin-plate 200 relative to the spinal cage might be angularly unrestricted, allowing as much as 360 degrees or more of rotation of the spin-plate 200 relative to the spinal cage 100. In general, the assembly may be such that when the spin-plate 200 is installed in the spinal cage 100, the interior of the spinal cage 100 is substantially open and unblocked except for the spin-plate 200.

The spin-plate 200 and the spinal cage 100 may be designed such that the spin-plate 200 can fit into the spinal cage 100 in only one configuration (as opposed to being able to fit into spinal cage 100 with either end of spin-plate 200 in either of the two grooves 150, 160). If the spinal cage comprises two grooves 150, 160 and the spin-plate 200 comprises two corresponding flat-to-flat dimensions, the two grooves 150, 160 can be of unequal dimensions and the flat-to-flat dimensions could be correspondingly different. As a result of this, the spin-plate 200 and the spinal cage 100 may fit together in only one configuration. The spin-plate 200 and the spinal cage 100 may be designed so that the at one end of the spin-plate 200, the flat-to-flat dimension of the shaft is slightly less than the width of groove 150, and at the other end of the spin-plate 200, the flat-to-flat dimension of the shaft is slightly less than the width of groove 160. It may be useful for mistake-proofing if the spin-plate 200 fits into the spinal cage 100 in only one configuration. Alternatively, the various components may be designed so that the spin-plate 200 can be placed into spinal cage 100 in either end-to-end configuration.

In general, an end of spin-plate 200 may have a non-circular cross-sectional shape having a minimum cross-sectional dimension and a maximum cross-sectional dimension. In order to enable sliding-in of a particular end of spin-plate 200 into a particular groove 150, 160, the minimum cross-sectional dimension of the end of spin-plate 200 may be less than the width of the particular groove. Following successful sliding-in, in order to allow rotation of an end of spin-plate 200 within opening 120 or opposed concave feature 130, the maximum cross-sectional dimension of the end of spin-plate 200 may be less than a transverse dimension of opening 120 or opposed concave feature 130.

Alternatively, it is possible that the two ends of shaft 200 and corresponding features of spinal cage 100 may be substantially identical to each other. In this situation, it may be possible to install spin-plate 200 into spinal cage 100 in a first orientation or in a second orientation in which the ends of spin-plate 200 are interchanged with each other. However, even in this situation the spin-plate need not be symmetric from end-to-end. For example, blade 230 might be located on shaft 210 at a location that is not the midpoint of shaft 210, and having the ability to insert spin-plate 200 into spinal cage 100 in two opposite end-to-end orientations would provide two choices for the position of the blade 230.

The spinal cage 100 and the spin-plate 200 may be such that the spin-plate 200 can be captured within spinal cage 100, at least for certain relative rotational positions. It is possible that when the spin-plate 200 is in the spinal cage 100, the spin-plate 200 could experience axial force from spinal cage 100 such as from elastic deformation of spinal cage 100. In this situation, it is possible that there could be a designed amount of axial force exerted by spinal cage 100 upon spin-plate 200, resulting in a designed amount of friction against rotation of spin-plate 200 relative to spinal cage 100 and essentially no permitted axial motion of spin-plate 200 relative to spinal cage 100. Alternatively, it is possible that the spin-plate 200 does not experience force exerted on it by spinal cage 100 along the rotational axis direction of spin-plate 200. The apparatus may be designed to lack such force if it is uncertain or unpredictable what the actual amount of such force would be. In such a structure, it is possible that there could be a slight amount of permitted axial motion (play) of the spin-plate 200 relative to spinal cage 100 along the rotational axis direction of spin-plate 200. Alternatively, the dimensions might be such that nominally there is substantially no permitted axial motion of spin-plate 200 relative to spinal cage 100 and also substantially no axial force exerted by spinal cage 100 upon spin-plate 200 along the direction of the axis of rotation of spin-plate 200. It is possible either for disc 290 to bear against an interior-facing surface of wall 110 or for blade 230 to bear against an interior-facing surface of wall 110, or both. It is possible that neither disc 290 nor blade 230 bears against an interior-facing surface of wall 110.

Geometrically, the spin-plate 200 can have two extreme points at least approximately corresponding to extreme ends of spin-plate 200 along the rotational axis of spin-plate 200. In the assembled configuration, where spin-plate 200 is installed in spinal cage 100, there can be a respective nearest-contact point of spinal cage 100 that is either touching or nearest to each of the respective extreme points of spin-plate 200. The distance between the two nearest-contact points can be greater than or approximately equal to the distance between the two extreme points of the spin-plate 200. For the case of creating friction due to axial loading on the spin-plate 200, the distance between the two nearest-contact points (when the spinal cage is undeformed) could be less than the distance between the two extreme points of the spin-plate 200.

The spinal cage 100 and the spin-plate 200 may be such that spinal cage 100 is capable of deflecting within an elastic limit, by an elastic deflection distance. In such a structure, everywhere along an insertion path of spin-plate 200 into spinal cage 100 there is a minimum clear dimension in a direction roughly corresponding to the axis of rotation of spin-plate 200. That minimum clear dimension plus an elastic deflection distance, is greater than the maximum overall length of spin-plate 200.

The spinal cage 100 and the spin-plate 200 may be such that the spin-plate 200 is capable of entering the spinal cage 100 and becoming trapped within spinal cage 100 while being able to rotate relative to spinal cage 100 after spin-plate 200 has become trapped within spinal cage 100.

Alternatively, the length of the spin-plate 200 could be such that the spin-plate 200 fits into spinal cage 100 without any interference along the axial dimension and is able to rotate without any friction caused by surfaces contacting each other forcibly along the lengthwise direction.

In embodiments of the invention, the ends of shaft 210 of spin-plate 200 may be flat-ended as illustrated or may have a convex curvature. Opening 150 and opposed concave feature 160 could be either flat-bottomed or concavely-curved.

In embodiments of the invention, the spin-plate 200 may be captured in the spinal cage 100 by one or both of two types of capturing action. It is possible that one of the capturing actions may be in effect even before the spin-plate 200 has been rotated away from the angular orientation that it has during insertion into spinal cage 100.

Another possibility is that there may be a capturing action that is in effect only for some rotational positions of spin-plate 200 relative to spinal cage 100 but not for other rotational positions. It is further possible that both types of capturing action may be present in the assembly.

In embodiments of the invention, the spin-plate 200 near at least one end may have at least one flat having a local flat external width of the spin-plate 200 relative to the flat, and the spinal cage may have at least one groove 150, 160 having a groove internal width, and the flat external width may be less than or equal to the groove internal width.

More generally, near at least one end the spin-plate 200 may comprise a non-circular cross-section having, at various lines passing through the spin-plate rotational axis perpendicular to the spin-plate rotational axis, a smallest cross-dimension and a largest cross-dimension. In such a situation, the spinal cage 100 may comprise a generally longitudinally-oriented groove 150, 160 having a groove width, and the groove width may be intermediate between the smallest cross-dimension and the largest cross-dimension. Groove width may refer to the minimum width dimension of the groove. For example, the spin-plate cross-section near at least one end of the spin-plate could be elliptical. The spin-plate cross-section near at least one end could be the cross-section of an enlargement 250, 252 or could be a cross-section of the shaft 210 itself of spin-plate 200.

In embodiments of the invention, the spin-plate 200 and the spinal cage 100 may cooperate to provide at least one detent position in the rotation of the spin-plate 200 with respect to the spinal cage 100. The detent may be such that rotation past the detent is permitted, but a certain amount of torque is necessary to pass the detent position, with that certain amount of torque being larger than the amount of torque needed to produce rotation in other portions of the rotational sequence. It is possible that there can be two detent positions in rotation of the spin-plate 200 with respect to the spinal cage 100. The two detent positions may separated by approximately 90 degrees of rotation, or by approximately 180 degrees of rotation. It is possible that a detent position can correspond to the deployed configuration of the spin-plate 200 relative to the spinal cage 100, in which blade 230 extends beyond spinal cage 100. It is possible that a detent position can correspond to the undeployed configuration in which blade 230 is contained within spinal cage 100. If there are two detent positions, it is possible that they can correspond to both of the just-described configurations.

In embodiments of the invention, it is also possible that the spin-plate 200 and the spinal cage 100 may cooperate to provide at least one stop position in rotation of the spin-plate 200 with respect to the spinal cage 100. In such a structure, when rotation reaches an appropriate position for the stop condition to come into effect, then the spin-plate 200 may become immobilized with respect to the spinal cage 100, it may become extremely difficult or impossible to rotate the spin-plate 200 beyond the stop angular position. It is possible that when the stop position is reached, it may still be possible to rotate the spin-plate 200 backward from the stop position. It is further possible that there may be a detent at the stop position, such that reverse rotation from the stop position requires overcoming a threshold amount of torque. It is still further possible that the spinal cage assembly could have a ratchet feature.

In embodiments of the invention, the spin-plate 200 and the spinal cage 100 may cooperate to provide an audible sound upon achievement of at least one particular angular position in rotation of the spin-plate 200 with respect to the spinal cage 100. The audible signal can come from some form of slippage of a member relative to another member. It is possible that a mechanism that provides some other described functionality, such as a detent or a rotational locking action, could also provide audible indication of an action or a condition. It is further possible that there can be tactile feedback that can be felt by the hand operating the tool or instrument that rotates the spin-plate 200. This tactile feedback can comprise, for example, a sharp change in the torque needed to rotate spin-plate 200 with respect to spinal cage 100. This tactile feedback can occur upon achievement of at least one particular angular position in rotation of the spin-plate 200 with respect to the spinal cage 100.

In embodiments of the invention, it is possible that the spinal cage 100 and the spin-plate 200 or other deployable member may have different radiopacities. For example, the spinal cage 100 may be made entirely or mostly of radiolucent material such as a polymer (for example, polyetheretherketone (PEEK)). If the spinal cage 100 is made of such a radiolucent material, the spinal cage 100 could additionally comprise radiopaque markers placed in it at desired locations. In such a situation, the spin-plate 200 could be made of or could comprise metal, with metals in general being at least somewhat radiopaque. As discussed elsewhere herein, it is possible that the spin-plate 200 could comprise subcomponents that themselves have differing radiopacities. For example, the shaft 210 and the blade(s) could be made of different materials having unequal radiolucency or radiopacity. It is possible that the spinal cage could comprise a majority of non-metallic material and the deployable member could comprise a majority of metal. For example, the spinal cage could be entirely polymeric material and the spin-plate 200 could be entirely metallic. The spin-plate 200 or blade or deployable member, or the spinal cage, could comprise features having known dimensions or spatial relationships or separation distances so as to be useful as reference and measurement markers for use during radiography.

In some embodiments of the present invention, spinal cage 100 and spin-plate 200 may comprise features that cooperate with each other to provide detents or stops involving the rotation of spin-plate 200 relative to spinal cage 100. Such features are illustrated in FIGS. 8, 9, 10, 19 and others.

In more detail, spinal cage 100 may comprise posts 190 that may protrude from the body of spinal cage 100 in an interior-facing direction. Spin-plate 200 may comprise geometric features that are appropriately located so as to interact with the posts 190. Spin-plate 200 may comprise disc 290, which may extend radially outward away from the longitudinal axis of shaft 210 of spin-plate 200. Disc 290 may comprise peaks or high regions that are more radially distant from the axis of spin-plate 200, and valleys or low regions that are closer to the axis of spin-plate 200. A peak or high region can include a plateau region having a substantially constant radial dimension, and a valley or low region also can include a region having a substantially constant radial dimension.

It is possible that the portion of post 190 that protrudes beyond the surface of wall 110 into interior space 112 of spinal cage 100 may have a taper. The taper may be such that the protruding part is larger in cross-section closer to the internal surface of wall 110, and is smaller in cross-section further from the internal surface of wall 110. The head 194 of post 190 may be frustoconical, although other shapes are also possible. As illustrated, the frusto-conical head 194 of post 190 has a total cone angle of 15 degrees or a half-angle of 7.5 degrees. This is illustrated in FIGS. 8, 9, 10 and others.

As illustrated in FIG. 10, disc 290 may comprise a series of a first valley, a second valley and a third valley. The angular interval from the center of the first valley to the center of the third valley may be approximately 90 degrees. The center of the second valley may be midway between the centers of the first valley and the third valley. The first valley and the third valley may be defined by inward curvatures having respective radii of curvature that may be equal to each other (labeled as R1). The second valley may be defined by another inward radius of curvature that is labeled as R2. The bottoms of first valley and third valley may be such that post 190 can approximately touch the bottoms of the first valley and the third valley, thereby providing a detent. The bottom of second valley may be such that there is clearance between posts 190 and the bottom of the second valley, thereby providing free rotation. The disc 290 may further comprise an external surface that is apart from the first-second-third valley sequence, which is defined by an outward curvature whose center of curvature is not located at the center of rotation of spin-plate 200.

It is also possible that the perimeter of disc 290 of spin-plate 200, or some portion of the perimeter of disc 290, can have a taper in a direction corresponding to the direction of taper of the head 194 of post 190. The angle of taper can be substantially equal to the half-angle of the frustoconical portion of post 190. However, the taper angles need not be identical to each other. It is not essential to have any taper on either of these components 190 or 290.

In describing the interaction of post 190 and disc 290 of spin-plate 200, it is useful to define a baseline distance from the center of rotation of spin-plate 200 to the nearest edge of the head 194 of post 190.

For achieving a detent, it is possible that a peak such as detent peak 292 may create a slight interference with post 190, but at the same time there may be appropriate elasticity in the spinal cage 100 or the spin-plate 200 or both so that upon application of a desired torque to spin-plate 200, detent peak 292 may slip past post 190. This can provide a detent action. Alternatively, it would also be possible to achieve a detent action with spring-loaded movable parts, living hinges, or by other means.

It is also possible that a peak such as stop peak 294 may interact with a post 190 so as to completely block further rotation of spin-plate 200 in a given direction beyond stop peak 294. The interference involving stop peak 294 may be such that it is not possible, using a reasonable amount of torque, to cause stop peak 294 to slip past post 190.

It is further possible to provide both a detent action and a stop action in close proximity to each other. In such a situation, rotation of spin-plate 200 may be able to occur freely in a certain range, and further rotation may involve passing a detent that requires a certain amount of torque to overcome. Upon passing this detent, there may be encountered a stop that completely prevents further rotation in that direction. When the components are in this described position, no additional forward rotation would be possible but rotation in the reverse direction would still be possible if suitable torque is exerted to pass the detent in the reverse direction.

FIG. 19 illustrates how the components can achieve certain detent and stop characteristics. As illustrated, stop peak 294 has a greater radial dimension than detent peak 292. Detent peak 292 and stop peak 294 may be sufficiently close together so that post 190 nestles in the valley between those two features and has little or no permitted rotation while located between those two features. In this configuration, while post 190 is between peaks 292, 294, there may be no rotation possible in a direction that would advance beyond peak 294 using any reasonable amount of torque, but there may be rotation possible in the reverse direction if sufficient torque is exerted to pass the detent involving detent peak 292.

It is also possible that there can be two detent peaks 292 in close proximity to each other so that when post 190 nestles between those two detent peaks 292, there is little or no permitted rotation. However, upon application of appropriate torque, it is possible to pass the detent in either direction of rotation.

It is possible that there may be a detent peak 292 plus a nearby detent peak 292 in close proximity to each other for a position that corresponds to the stowed position of spin-plate 200 in which deployable elements do not protrude from spinal cage 100, as may be used during the initial implantation action. There may also be a detent peak 292 along with a nearby stop peak 294 in close proximity to each other for a position that corresponds to the deployed position of spin-plate 200 in which deployable elements protrude from spinal cage 100, as may be used during the final part of implantation. The undeployed (stowed) position and the deployed position may be separated from each other by approximately 90 degrees of rotation. In the illustrated configuration, at the stowed position, there is a detent action, and at the deployed position, there is a detent with stop action. The detent plus stop action prevents rotation of the spin-plate further than the deployed position.

It is possible to have more than one detent or more than one stop such that the same detent action or stop action is created simultaneously at two different locations around the perimeter of disc 290. This may be achieved in conjunction with having two posts 190. These two locations of posts 190 may be separated from each other by approximately 180 degrees of angular position. The described configuration of two detent peaks 292 in close proximity to each other may occur at two places around the disc 290. Similarly, the described configuration of a detent peak 292 in close proximity to a stop peak 294 may occur at two places around the disc 290. The use of such duplicative configurations may provide redundancy. If there is a plurality of detent peaks 292, the various detent peaks 292 may be geometrically identical to each other, but they do not have to be. If there is a plurality of stop peaks 294, the various stop peaks 294 may be geometrically identical to each other, but they do not have to be.

Figure 19A:
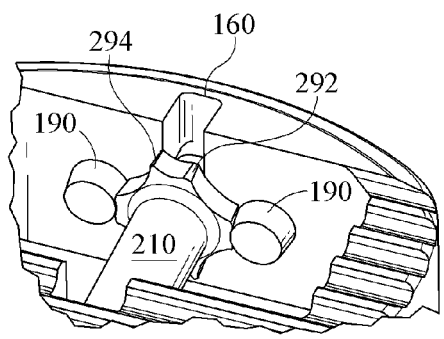
Figure 19B:
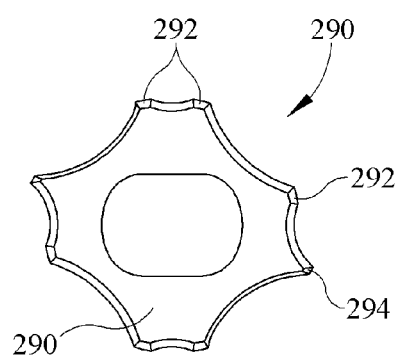
Figure 19C:
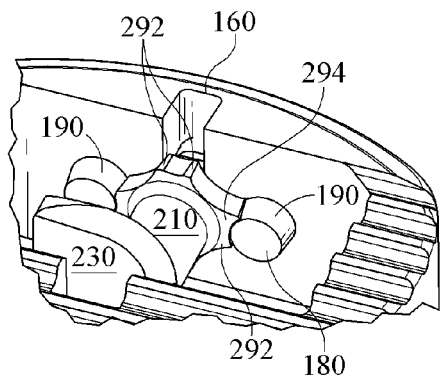
Figure 19D:
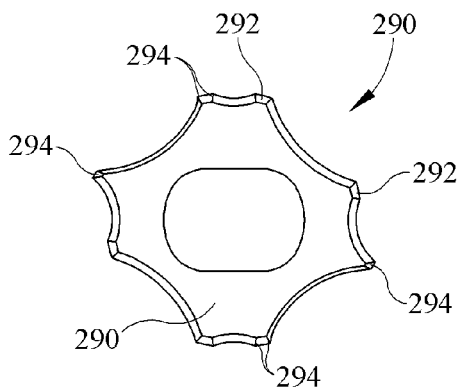

FIG. 19*b* illustrates another possible shape of disc 290. In this spin-plate there is an especially tall stop peak 294. FIG. 19*a* illustrates the same also showing the positions of post 190 when the spin-plate is in position such that blade is undeployed (neutral position). A configuration such as this can ensure that rotation away from the stowed position is only possible in one direction of rotation, and also that the rotation encounters a well-defined stop at the intended end of rotation. At the stowed position, there is a detent action with a stop that prevents the spin-plate from rotating further in the reverse direction than the stowed position. In the configuration of FIG. 19*c* at the deployed position, there is a detent with stop action that prevents rotation of the spin-plate 200 further than the deployed position.

Referring now to FIGS. 9, 10, 18, and 19, the disc 290 may comprise a series of three valleys that govern motion over a rotational interval of 90 degrees. This same pattern may be repeated 180 degrees away on the disc 290. The first valley may be where post 190 nestles in the stowed position of blade 230. The third valley maybe where post 190 nestles in the deployed position of blade 230. The bottom of the first valley and the bottom of the third valley may be separated from each other by 90 degrees of rotation. The bottom of the first valley and the bottom of the third valley may be at the same radial distance from the axis of rotation of spin-plate 200, although they do not have to be. The bottom of the second valley may be deeper (at a smaller radial distance from the axis of rotation) than the bottom of the first and third valleys, which could allow for relatively free rotation of spin-plate 200 during much of the rotation from the stowed position to the deployed position. However, it is not essential that the bottom of the second valley be deeper than the bottom of the first and third valleys. At the edge of third valley that is beyond the position that post 190 would travel in during the nominal 90 degrees of rotation, i.e., that is away from first and second valleys, the wall of the third valley may rise higher than does the wall of the first valley on the side of the first valley that is away from second and third valleys. This extra wall height may provide an especially secure stop action to prevent the spin-plate from rotating beyond the desired 90 degrees of rotation. The described side of first valley may be high enough to provide a detent action, but not as high as the described height of the third valley wall, in order to help allow the spin-plate to slide into position through the groove 160.

Both the anterior tip of the spin-plate 200 and the posterior tip of the spin-plate 200 may have a pair of opposed flats, and sliding-in to the grooves in spinal cage 100 may be guided by using the flat. After the spin-plate 200 has slid through the grooves 150, 160 and into opening 120, opposed concave feature 130 suitably far that it is able to rotate, and after a small amount of rotation has taken place, one or both tips of spin-plate 200 may become trapped in opening 120 or opposed concave feature 130 thereby resisting any force that might tend to dislodge spin-plate 200 from that position.

Referring now to FIGS. 20-25, the installation tool may have construction comprising two or three members that are at least approximately coaxial with each other and are nested within each other. The outermost member may, at its distal end, engage a spinal cage 100. The spinal cage 100 may be a spinal cage or the like. As illustrated in FIG. 21, a portion of the installation tool such as the outermost member of the installation tool may, for example, comprise a protrusion that is suitable to engage an external feature of spinal cage 100 such as instrumentation groove 174. Another member of the installation tool, such as the intermediate member of the installation tool, may, at its distal end, engage an instrumentation interface feature of spinal cage 100. For example, this member may comprise, at its distal end, threads that may be capable of engaging corresponding threads on spinal cage 100, such as threads in openings 172*a*, 172*b*, 172*c*, 172*d*. Taken together, these two members may engage spinal cage 100 so as to provide a substantially rigid connection between the installation tool and spinal cage 100. One of the members may have a thumbwheel at or near its proximal end.

The installation tool may further comprise a member that, at its distal end, is capable of interfacing with spin-plate 200, which may be rotatable with respect to spinal cage 100. This member, which may be referred to as a locker tool, may be insertable into the rest of the installation tool or removable therefrom, as desired. It is possible that when the locker tool is not in its operable position, the remaining part of the installation tool may be capable of being struck by a hammer. FIG. 23 illustrates a locker tool by itself. FIG. 24 illustrates such a tool ready to be inserted in the installation tool.

It is still further possible that the mechanism for causing rotation of the spin-plate 200 may have some portion that is permanently part of the installation tool and some other portion that is connected to the installation tool only when desired. The innermost member may comprise a first part and a second part. The first part may be capable of engaging with and rotating spin-plate 200. The second part may be connectable to the first part and may comprise a handle. The second part may be removable from the installation tool. When the second part is absent from the installation tool, the installation tool may be capable of being struck on its proximal end by a hammer or similar device, while the installation tool is engaged to spinal cage 100.

It is possible that a handle or other feature of the locker tool (or more generally any device that causes rotation of the spin-plate 200) may indicate the position of the blade 230 of spin-plate 200, such as by being parallel with the blade 230 of spin-plate 200. FIG. 25*a* shows a spinal cage assembly together with the installation tool and locker tool, in a configuration such that the blade 230 is in a neutral or undeployed position. As illustrated, blade 230 and the handle of the locker tool are substantially parallel to each other in a substantially horizontal orientation. FIG. 25*b* shows the same apparatus in a deployed or engaged configuration. Again, blade 230 and the handle of the locker tool are substantially parallel to each other, but in this illustration both have a substantially vertical orientation. These illustrations illustrate the configuration that would be used for an anterior surgical approach.

The insertion tool may be either combined with or separate from a rotational tool that may be used for rotating the spin-plate 200. The handle of the tool for rotating the spin-plate 200 could be parallel to the long direction of the spin-plate 200. This could provide a direct indication to the surgeon of the position of the spin-plate 200.

It is possible that the installation tool may comprise limits on rotation of the innermost member, relative to other parts of the installation tool. The installation tool may be designed and constructed such that, when the installation tool is engaged with spinal cage 100, the initial rotational limit or the final rotational limit or both may substantially correspond to the situation in which spin-plate 200 is at a rotational detent or a rotational stop that may be built into the relationship between spin-plate 200 and spinal cage 100 when spin-plate 200 is installed in spinal cage 100. It is further possible that the installation tool may comprise a ratchet such as to determine that only one direction of rotation is allowable, rather than both directions of rotation.

Referring now to FIGS. 20-25, in some embodiments of the present invention, there may be provided an installation tool 710 that mates to spinal cage (100) and has a central passageway 715 able to accept a rotational tool 720 for rotating spin-plate 200. The installation tool 710 that mates with spinal cage 100 may be physically separate from the rotational tool 720 that is used to rotate spin-plate 200 and may be able to be used independently of the rotational tool 720 that is used to rotate spin-plate 200. It is possible to insert spin-plate rotation tool 720 through the bore 715 of installation tool 720 at desired times and to remove spin-plate rotation tool 720 from the bore 715 of installation tool 710 at other times when it is not desired to use the tools together. For example, in some embodiments of the present invention, there may be times when the spinal cage 100 is implanted without containing spin-plate 200. In such instance, there is no need for spin-plate rotation tool 720. In other situations, when the spin-plate 200 is in the spinal cage 100, there still may be times during surgery when there is no need for the presence of the spin-plate rotation tool 720, and so the spin-plate rotation tool 720 can be absent at those times. Such absence may free up the bore of the installation tool 710 for other purposes.

Furthermore, in some embodiments of the present invention, it is possible that the instrumentation used for causing rotation of spin-plate 200 may be designed such that the instrumentation itself only allows the designated amount of rotation, such as 90 degrees, and the instrumentation makes it impossible to over-rotate spin-plate 200 beyond that designated amount of rotation beyond the designated amount of rotation.

FIGS. 22*a*, 22*b*, 22*c*, 22*d* illustrate the assembly of an installation tool to the spinal cage 100 in for different orientations for four different surgical approaches.

An embodiment of the invention comprises a kit containing at least one spinal cage 100 and at least one spin-plate 200 suitable to fit into at least one of the spinal cages 100. It is possible that various spinal cages 100 in the kit may differ from each other in lordosis angle, in overall dimensions, or any other respect. However, it is also possible that even if various spinal cages 100 differ from each other in some respect, all or some of the spinal cages 100 could still be identical in those dimensions or features that affect the interaction of spin-plate 200 with spinal cage 100. It is possible that various spin-plates could differ from each other in the position of the blade 230 on shaft 210, such as the position of blade 230 in the direction along the length of the blade 230. In such a situation, the spin-plate 200 could be chosen at or around the time of surgery based on what location within the bone (cortical bone as compared to cancellous bone, or how far into the bone in a direction along the anterior-posterior direction that is the axis of rotation of spin-plate 200) it is desired that the spin-plate 200 interact with. The kit and its components could be made such that more than one spin-plate 200 is suitable to be used with a particular spinal cage 100. For example, it is possible that a particular spinal cage could accept more than one choice of spin-plate 200, each of which might have different tip-to-tip length of blade 230, thereby providing choices as to the distance of penetration of blade 230 into adjacent vertebrae.

The kit may further comprise tools for installing, measuring or other capabilities. If any tools are associated with placing the spin-plate 200 into spinal cage 100, such tools can be included in the kit.

Some embodiments of the present invention may comprise a filler piece 600 suitable to occupy a large fraction of the open space in the interior of spinal cage 100 that is not already occupied by the spin-plate 200. This is illustrated in FIG. 26. If the spinal cage 100 is used with spin-plate 200, the filler piece 600 may have empty spaces suitable to accommodate any permissible rotational position of spin-plate 200.

Geometrically, the filler piece 600 may be dimensioned such that when the filler piece 600 is in place, the filler piece 600 does not occupy any space occupied by the shaft 210 of the spin-plate 200 and also does not occupy any space occupied by the blade 230 of the spin-plate 200 in any of the positions that the spin-plate 200 either is permitted to occupy or passes through during permitted rotation. It is still possible that the filler piece could occupy certain space that is in the plane of rotation of spin-plate blade 230 but is located at rotational angles where the blade never goes. Also, the filler piece 600 may be dimensioned such that when the filler piece 600 is in place, the filler piece 600 does not occupy any space occupied by the disc 290 that may be near the posterior end of the shaft 210 of the spin-plate 200.

The filler piece 600 may comprise a slot 610 opening to one of the end face surfaces of the filler piece 600. Slot 610 may have a width at least as large as the diameter of the shaft 210 of the spin-plate 200. The geometry of the slot 610 and the other dimensions of the filler piece 600 may be such that when the spin-plate 200 is in place in spinal cage 100 and the filler piece 600 is in place in spinal cage 100, the end face surfaces 620 of the filler piece 600 may at least approximately align with end surfaces of the spinal cage 100 itself.

Regarding other surfaces of filler piece 600, the filler piece 600 may be such that when the filler piece 600 is in place in spinal cage 100, a posterior face 630 of the filler piece 600 touches an internal posterior surface of spinal cage 100. The filler piece 600 may further be such that when the filler piece 600 is in place in the spinal cage 100 with the posterior face 630 touching internal posterior surface of spinal cage 100, filler piece 600 does not interfere with the spin-plate 200 or blade 230 in any of the permitted positions of rotation. The location of filler piece 600 may be defined in part by having the front surface of filler piece 600 touch blade 230 or be able to fit between blade 230 and the internal posterior surface of spinal cage 100. Alternatively, there may be constraints such that filler piece 600 contacts the interior of spinal cage 100 in such a way that insert 600 is constrained against moving into any position that would result in interference with spin-plate 200 or blade 230. For example, the constraint may be such that filler piece 600 cannot advance sufficiently far anteriorly even to touch blade 230. For example, a portion of a front surface 640 of filler piece 600 may interact with an internal surface of spinal cage 100 so as to insure that there is some empty space between filler piece front surface 640 and the corresponding internal surface of spinal cage 100. It is possible that filler piece 600 could be shaped so that when posterior face 630 touches internal posterior surface of spinal cage 100, a portion of anterior face of filler piece 600 touches or nearly touches an internal anterior surface of spinal cage 100, in a place that is not within the range of motion of blade 230 in any of the permitted positions of blade 230.

Filler piece 600 may further comprise a recess 690 suitable to accommodate a disc 290 on spin-plate 200. For example, recess 690 may be a groove.

The filler piece 600 may be porous and conducive to bone ingrowth. The filler piece 600 may be substantially rigid or alternatively may have some property of elasticity or ability to be squeezed. The filler piece 600 may be osteoconductive, such as comprising a member of the calcium phosphate family and having pores of appropriate size. The filler piece 600 may further be osteoinductive, such as comprising any of a number of known osteoinductive substances, such as but not limited to demineralized bone matrix, bone morphogenetic protein, and other known substances. The filler piece 600 may contain blood, bone marrow, platelet rich plasma, or other such substances. The filler piece 600 may be resorbable and may comprise one or more resorbable polymers and may comprise a resorbable or nonresorbable ceramic.

The filler piece 600 may be resilient, such as a filler piece 600 that comprises particles of ceramic joined by films of a polymeric material that is at least somewhat resilient. The filler piece 600 may be slightly larger in the longitudinal direction than the corresponding dimension of spinal cage 100 so that when an assembly of a spinal cage 100 and filler piece 600 is implanted in a patient, the filler piece 600 establishes contact against endplate or bone of vertebrae. The ability of a resilient filler piece 600 to compress may allow the assembly comprising spinal cage 100 and filler piece 600 to be installed so that the filler piece 600 is slightly in compression between the vertebrae. That compression may help to maintain contact between the vertebral endplate and the filler piece 600, aiding in ingrowth of bone into the filler piece 600. It is also possible that the filler piece 600 may be in compression between certain surfaces of the interior of the wall 110 of spinal cage 100. This may help to keep the filler piece 600 in place relative to the spinal cage 100 during implantation or other steps.

It is possible for a kit to contain a first filler piece 600 suitable to be used when a spin-plate 200 is installed in spinal cage 100, and also a second different filler piece suitable to be used if spinal cage 100 is installed without containing a spin-plate 200. In this way, the filler piece 600 used in the presence of a spin-plate 200 provides a maximum amount of filler or bone growth promoting material that can be used under the circumstances when a spin-plate 200 is present, and for the situation where no spin-plate is present, the internal cross-section of the spinal cage 100 can be essentially completely filled with a different filler piece.

It is possible that the filler piece 600 may have a specific color. In order to accomplish this, the filler piece 600, at one of the last stages of manufacturing, may be wetted with a solution containing a biocompatible dye. Then, the solvent of that solution may be allowed or caused to evaporate, leaving the dye behind in filler piece 600. The solution may be aqueous, or may be based on an organic solvent such as ethanol, or could contain both water and an organic solvent such as ethanol. The dye may be a dye that is water-soluble, or organic-solvent-soluble, or both. The solution could also comprise a surfactant. It is furthermore possible that the coloration could be applied only to specific regions of the filler piece 600, rather than everywhere.

A surgeon may be provided with a set of spinal cages and installation tools any or all of which may use color-coding. Color-coding of metal parts such as spin-plates 200 or instrument tips may be achieved by anodizing or other surface treatment. Color-coding of polymeric parts such as spinal cages 100 may be achieved by additives during molding. Color-coding of filler pieces 600 may be achieved as described.

For example, a spinal cage 100 and the filler piece 600 intended for that spinal cage 100 may have identical or similar colors.

In some embodiments of the present invention, the spinal cage 100 may comprise a radiopaque marker that also interacts with a deployable element or a rotatable element such as spin-plate 200. For example, the radiopaque marker may be a post 190 that may be involved in creating a detent function or a stop function or both involving rotation of spin-plate 200. Post 190 is illustrated in FIG. 8. The radiopaque marker may be more radiopaque than other parts of the spinal cage 100. It is further possible that there may additionally be other radiopaque markers present in spinal cage 100 that do not interact with a deployable or rotatable element such as spin-plate 200. Radiopaque markers may be located so as to assist in interpreting radiographic images and may be located in more than one plane or direction. For example, post 190 may be made of or may comprise a material having a desired radiopacity.

Some embodiments of the present invention can include a trial piece that may be geometrically similar to the actual spinal cage but not intended to remain inside a patient. A trial piece may comprise a spin-plate 200 with a blade 230 similar to those in the actual spinal cage assembly. It is possible that a trial piece could have a blade 230 that is stronger than the blade 230 in the actual spinal cage assembly.

It is possible that a trial piece could be made out of metal rather than the polymeric material that might be used for the actual spinal cage 100. It is also possible that a trial piece might have smooth vertebra-facing surfaces rather than having grooves or teeth as might be present on the actual spinal cage 100. Such a lack of teeth might make it easy to remove the trial piece when it is time to implant the actual spinal cage 100.

A trial piece could be used if a deployable element such as a blade 230 is resorbable, which brings the possibility that a resorbable blade 230 might not be as strong as a blade made of metal. This might create an incentive to use a separate trial piece to cut a slot in the bone. For example, a trial piece that is made completely out of metal including the blade could be stronger than the actual spinal cage assembly and might be capable of receiving more torque or exerting more cutting force than the actual spinal cage assembly. It would be possible to use such a trial piece to pre-cut a slot that may be the interface for the actual spinal cage. Then, the trial piece could be removed and the actual spinal cage assembly could be implanted appropriately located so that the blade 230 of the actual spinal cage enters the slot in bone created by the blade of the trial piece.

Some embodiments of the present invention can comprise the surgical method described herein. The method can include: implanting a trial piece having a trial piece deployable member; deploying the trial piece deployable member so as to displace or remove bone to form a cavity; retracting the trial piece deployable member; removing the trial piece; implanting a spinal cage assembly having a deployable member; and deploying the deployable member to occupy at least a portion of the cavity created using the trial piece.

Some embodiments of the present invention comprise a surgical method.

It is described elsewhere herein that one possible surgical approach for implantation of the described spinal cage assembly is an anterior approach. However, it is also possible that the spinal cage assembly could be implanted using a surgical approach that is other than an anterior approach. For example, the approach for implanting the spinal cage assembly could be lateral or anterolateral. However, even if spinal cage assembly is implanted via some surgical approach other than anterior, the axis of rotation of spin-plate 200 may still be anterior-posterior. Therefore, causing the spin-plate 200 to rotate into a desired angular position may involve accessing a feature that is on an anterior surface of the spinal cage 100, which may require some use of an anterior approach.

A surgical method may comprise using two separate incisions as illustrated in FIG. 27. The incision for implanting the spinal cage assembly may be an incision using an approach other than an anterior approach and may be the larger of the two incisions. The incision for causing rotation of spin-plate 200 may be the smaller of the two incisions and may be an anterior approach. For example, the spinal cage assembly may be installed using an anterolateral or lateral approach, and then for purpose of causing rotation of spin-plate 200, a small incision using approximately an anterior approach may be created to provide access for a rotational tool.

FIGS. 28 and 29 illustrate spinal cage assemblies that contain gears to re-orient rotational motion delivered to the spinal cage assembly by a tool. In FIG. 28 there is a worm gear, and in FIG. 29 there is a bevel gear.

Although a spin-plate 200 has been described, more generally, an embodiment of the invention could comprise any deployable element that can optionally be used with a spinal cage. Rotation is not the only possible motion that could be used to deploy a deployable member that is optionally usable with the spinal cage 100. For example, the design could be such as to use a translational motion for deploying a deployable member.

It is possible to practice embodiments of the invention without groove 150, 160. The spin-plate may be designed to exploit a mechanical/interference mode of retention without the need to cut into bone. In such an embodiment the spin-plate could be merely asymmetric in its central cross section such that when rotated into position its vertical height extends more fully into the height of contour of the concavities of the vertebral endplates and establishes a significant degree of mechanical interference that enhances the retention against expulsive forces that might tend to expel the spinal cage assembly from its desired position between the vertebrae.

All referenced documents are incorporated by reference herein in their entirety. Features described herein may be combined in any combination, and steps of a method may be performed in any sequence that is physically possible. Although embodiments of the present invention have been described herein, it is desired that the scope be limited only by the scope of the following claims.

The invention claimed is:

1. A spinal cage comprising:
   a wall having an internal surface and an external surface, both extending vertically and generally parallel to a vertical axis of said spinal cage and progressing circumferentially, wherein said external surface forms a closed circumference, and wherein said internal surface forms a closed perimeter defining an interior space;

wherein said internal wall surface comprises at least a first internal groove within said internal wall surface, said groove extending vertically at least approximately parallel to said vertical axis;

wherein said first internal groove has two respective side walls opposed to each other and generally parallel to each other, said two respective side walls defining a groove width therebetween, said first internal groove having a groove base surface connecting between said side walls;

wherein at a first vertical end of said first internal groove, said side walls extend as far as said wall extends vertically;

wherein at an opposed vertical end of said first internal groove, said side walls connect with a curved surface within said internal wall surface, said curved surface defining a cylindrical space within said internal wall surface having a cylindrical diameter; and wherein said cylindrical diameter is greater than said groove width and said cylindrical space is centered midway between said side walls.

2. The spinal cage of claim 1, wherein said first internal groove extends through from one end surface of said spinal cage but does not extend through to an opposed end surface of said spinal cage.

3. The spinal cage of claim 1, wherein said first internal groove extends through from one end surface of said spinal cage through to an opposed end surface of said spinal cage.

4. The spinal cage of claim 1, wherein said first internal groove comprises an entrance feature.

5. The spinal cage of claim 1, further comprising:
a second internal groove.

6. The spinal cage of claim 5, wherein said first and said second internal grooves are parallel to each other.

7. The spinal cage of claim 5, wherein said second internal groove has a second groove width, and said first groove width is unequal to said second groove width.

* * * * *